(12) United States Patent
Noji et al.

(10) Patent No.: US 9,237,877 B2
(45) Date of Patent: Jan. 19, 2016

(54) THORACIC DIAGNOSIS ASSISTANCE SYSTEM AND COMPUTER READABLE STORAGE MEDIUM

(71) Applicant: KONICA MINOLTA, INC., Chiyoda-ku, Tokyo (JP)

(72) Inventors: Syou Noji, Tachikawa (JP); Tetsuo Shimada, Hino (JP); Shintaro Muraoka, Hachioji (JP); Sumiya Nagatsuka, Hino (JP)

(73) Assignee: KONICA MINOLTA, INC. (JP)

( * ) Notice: Subject to any disclaimer, the term of this patent is extended or adjusted under 35 U.S.C. 154(b) by 0 days.

(21) Appl. No.: 14/556,410

(22) Filed: Dec. 1, 2014

(65) Prior Publication Data

US 2015/0092911 A1 Apr. 2, 2015

Related U.S. Application Data

(63) Continuation of application No. 13/819,195, filed as application No. PCT/JP2011/055524 on Mar. 9, 2011.

(30) Foreign Application Priority Data

Aug. 27, 2010 (JP) .................................. 2010-190241
Jan. 26, 2011 (JP) .................................. 2011-013538

(51) Int. Cl.
*G06K 9/00* (2006.01)
*A61B 6/00* (2006.01)
(Continued)

(52) U.S. Cl.
CPC .................. *A61B 6/50* (2013.01); *A61B 5/0205* (2013.01); *A61B 5/08* (2013.01); *A61B 5/113* (2013.01); *A61B 6/4035* (2013.01); *A61B 6/463* (2013.01);
(Continued)

(58) Field of Classification Search
None
See application file for complete search history.

(56) References Cited

U.S. PATENT DOCUMENTS

2002/0126800 A1* 9/2002 Matsumoto et al. .......... 378/154
2003/0190064 A1 10/2003 Inoue
(Continued)

FOREIGN PATENT DOCUMENTS

JP 63168152 A 12/1988
JP 1098587 A 4/1998
(Continued)

OTHER PUBLICATIONS

Notification of Refusal for corresponding Japanese Patent Application No. 2012-530550; mailing date Nov. 18, 2014; with English translation.
(Continued)

*Primary Examiner* — Hadi Akhavannik
(74) *Attorney, Agent, or Firm* — Cantor Colburn LLP

(57) ABSTRACT

Provided is a thoracic diagnosis assistance system. The system includes, an imaging unit, an extracting unit, a region dividing unit, an analysis unit and a display unit. The extraction unit extracts a lung field region from the plurality of successive image frames generated by the imaging unit. The region dividing unit divides the lung field region extracted by the extraction unit into a plurality of sub-regions and correlates the sub-regions among the plurality of image frames. The analysis unit performs an analysis of the sub-regions to calculate an inspiratory feature quantity and an expiratory feature quantity and to calculate a value of a ratio of the calculated inspiratory feature quantity to expiratory feature quantity and creates a histogram of the calculated ratio value. The display unit displays the histogram.

5 Claims, 20 Drawing Sheets

(51) Int. Cl.
*A61B 5/08* (2006.01)
*G06T 7/00* (2006.01)
*A61B 5/113* (2006.01)
*A61B 5/0205* (2006.01)

(52) U.S. Cl.
CPC ............. *A61B 6/5217* (2013.01); *G06T 7/0016* (2013.01); *A61B 6/4233* (2013.01); *A61B 6/5235* (2013.01); *A61B 6/563* (2013.01); *G06T 2200/24* (2013.01); *G06T 2207/10016* (2013.01); *G06T 2207/10116* (2013.01); *G06T 2207/20021* (2013.01); *G06T 2207/30061* (2013.01)

(56) References Cited

U.S. PATENT DOCUMENTS

| | | | |
|---|---|---|---|
| 2003/0190067 | A1 | 10/2003 | Tsujii |
| 2004/0082874 | A1 | 4/2004 | Aoki et al. |
| 2004/0101107 | A1* | 5/2004 | Watanabe ............... 378/154 |
| 2007/0242794 | A1* | 10/2007 | Stanton ............... A61B 6/02 378/5 |
| 2010/0239145 | A1* | 9/2010 | Fujita ............... A61B 6/4441 382/131 |
| 2010/0246925 | A1 | 9/2010 | Nagatsuka |

FOREIGN PATENT DOCUMENTS

| | | |
|---|---|---|
| JP | 2004312434 A | 11/2004 |
| JP | 2005312775 A | 11/2005 |
| JP | 2006020716 A | 1/2006 |
| JP | 2006043200 A | 2/2006 |
| JP | 2009273671 A | 11/2009 |
| JP | 2010069099 A | 2/2010 |
| WO | 2006137294 A1 | 12/2006 |

OTHER PUBLICATIONS

International Preliminary Report on Patentability; International Application No. PCT/JP2011/055524; Date of Issuance: Mar. 19, 2013; 14 pages, with English translation.

International Search Report for International Application No. PCT/JP2011/055524; Date of Mailing: May 17, 2011, with English translation.

U.S. Notice of Allowance corresponding to U.S. Appl. No. 13/819,195; Date of Mailing: Jan. 30, 2015.

\* cited by examiner

FIG.8C
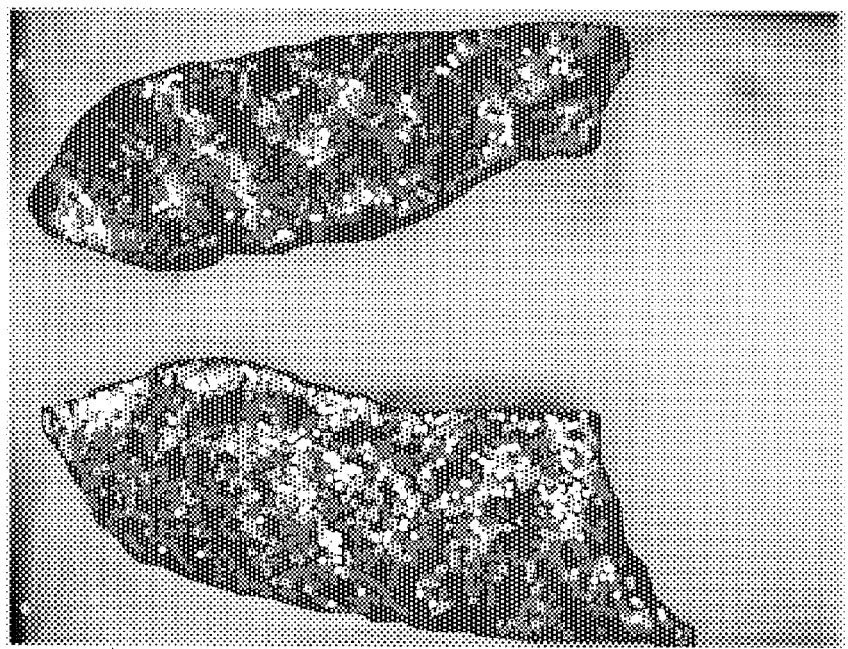
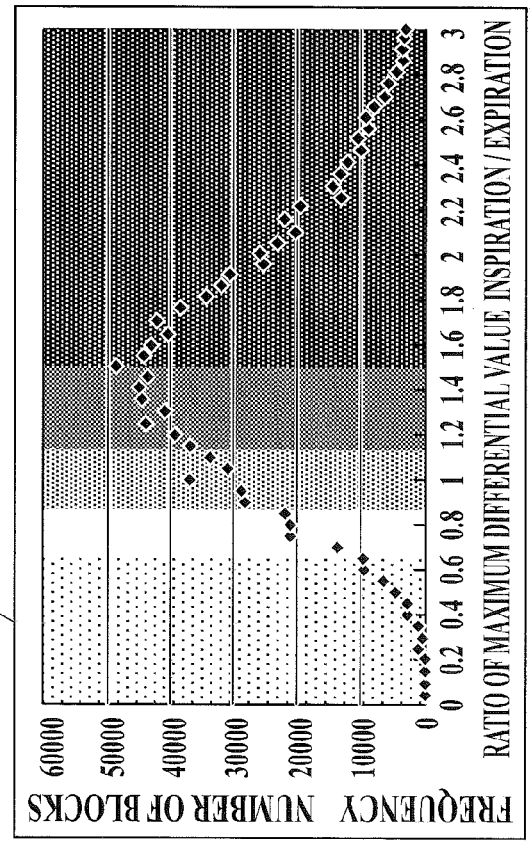

FIG.17
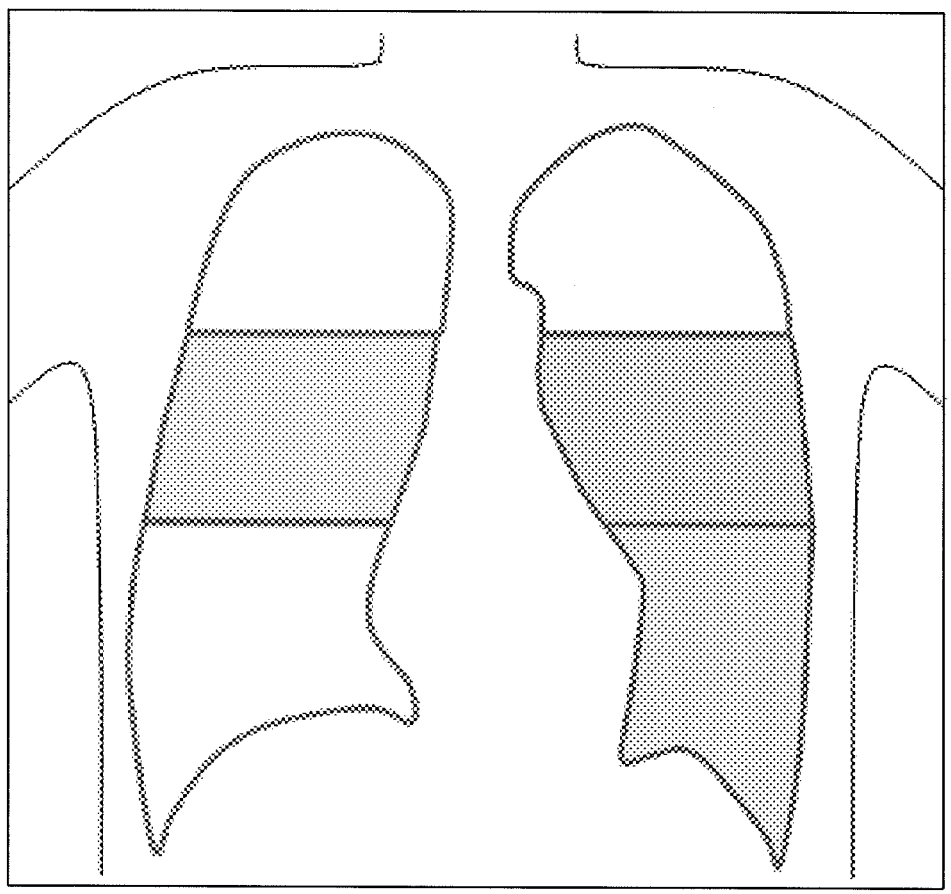
VARIATION COEFFICIENT LOW          VARIATION COEFFICIENT HIGH

US 9,237,877 B2

THORACIC DIAGNOSIS ASSISTANCE SYSTEM AND COMPUTER READABLE STORAGE MEDIUM

CROSS REFERENCE TO RELATED APPLICATIONS

The present application is a continuation application of U.S. patent application Ser. No. 13/819,195, filed on Feb. 26, 2013, the entire contents of which are incorporated herein by reference and priority to which is hereby claimed. The 13/819,195 application is a U.S. National Stage of Application No. PCT/JP2011/055524, filed on 9 Mar. 2011. Priority under 35 U.S.C. §119(a) and 35 U.S.C. §365(b) is claimed from Japanese Application No. 2010-190241, filed 27 Aug. 2010, and Japanese Application No 2011-013538, filed 26 Jan. 2011, both disclosures of which are also incorporated herein by reference.

TECHNICAL FIELD

The present invention relates to thoracic diagnosis assistance system and program.

BACKGROUND ART

Instead of conventional static imaging by radiation and diagnosis of the chest portion using film/screen or photo-stimulable phosphor imaging plates, there are some attempts to use semiconductor image sensors such as FPDs (flat panel detectors) for imaging dynamic images of the chest portion and applying the images to diagnosis. Specifically, by using the quick response of semiconductor image sensors in the process of reading and erasing image data, pulses of radiation are successively delivered from a radiation source in synchronization with read and erase timing of the semiconductor image sensors to perform imaging several times per second, thus imaging the movement of the chest portion. The series of images acquired by the imaging are sequentially displayed, thus allowing physicians to observe a series of movement of the chest portion associated with breathing movements, heartbeats, or the like.

Various techniques are proposed which extract information useful for diagnosis from dynamic images of the chest portion. For example, Patent Document 1 describes a technique to generate difference images representing differences in pixel value between plurality of image frames constituting a dynamic image and calculate maximum values (average values, intermediate values, or the like) of the pixel values from the generated difference images for display thereof.

PRIOR ART DOCUMENT

Patent Document

Patent Document 1: Japanese Patent Laid-open Publication No. 2004-312434

DISCLOSURE OF THE INVENTION

Problems to be Solved by the Invention

However, only by calculating and displaying the maximum values (average values, intermediate values, or the like) of the differences between the frames as described in Patent Document 1, it is difficult for physicians other than skilled respiratory physicians to grasp clinical features (case names).

An object of the present invention is to provide physicians with information that facilitates grasping the clinical features of ventilation of lung fields and is effective for diagnosis. Specifically, an object of the present invention is to provide diagnostic information with which appropriate diagnosis can be made by physicians with little practical experience in using stethoscopes.

Means for Solving the Problem

To solve the aforementioned problems, according to a first aspect of the present invention, there is provided a thoracic diagnosis assistance system, including:

an imaging unit which images chest portion movements in at least one breathing cycle and which generates a plurality of successive image frames;

an extraction unit which extracts a lung field region from each of the plurality of image frames generated by the imaging unit;

a region dividing unit which divides the lung field region extracted by the extraction unit into a plurality of sub-regions and which correlates the sub-regions among the plurality of image frames;

an analysis unit which performs an analysis for each of the sub-regions correlated in the plurality of image frames to calculate an inspiratory feature quantity and an expiratory feature quantity of the sub-region and to calculate a value of a ratio of the calculated inspiratory feature quantity to expiratory feature quantity and which creates a histogram of the calculated ratio value; and a display unit which displays the histogram created by the analysis unit.

Preferably, the inspiratory feature quantity is a maximum value of an absolute value of inter-frame difference values obtained by calculating a difference in pixel signal values between the image frames chronologically adjacent among a group of the image frames corresponding to an inspiratory period, and the expiratory feature quantity is a maximum value of an absolute value of inter-frame difference values obtained by calculating a difference in pixel signal values between the image frames chronologically adjacent among a group of the image frames corresponding to an expiratory period.

Preferably, the inspiratory feature quantity is a number of image frames corresponding to the inspiratory period in one breathing cycle, and the expiratory feature quantity is a number of image frames corresponding to the expiratory period in one breathing cycle.

Preferably, the inspiratory feature quantity is a maximum value of a pixel signal value in the plurality of image frames of one breathing cycle, and the expiratory feature quantity is a minimum value of a pixel signal value in the plurality of image frames in one breathing cycle.

Preferably, the region dividing unit divides the lung field region of one image frame among the plurality of image frames into a plurality of sub-regions, divides the lung field region of each of the other image frame into sub-regions located at the same pixel positions as the respective sub-regions of the one image frame, and correlates the sub-regions at the same pixel positions among the plurality of image frames.

Preferably, the region dividing unit divides the lung field region of one image frame among the plurality of image frames into a plurality of sub-regions, extracts a region highly matching with the sub-regions in the one image frame from each of the other image frame, divides the lung field region of each of the other image frame to the extracted regions, and correlates the sub-regions highly matching with each other among the plurality of image frames.

Preferably, the imaging unit performs dynamic imaging without using a grid.

According to a second aspect of the present invention, there is provided a program causing a computer to function as:

an extraction unit which extracts a lung field region from each of a plurality of image frames representing chest portion movements in at least one breathing cycle;

a region dividing unit which divides the lung field region extracted by the extraction unit into a plurality of sub-regions and which correlates the sub-regions among the plurality of image frames;

an analysis unit which performs an analysis for each of the sub-regions correlated in the plurality of image frames to calculate an inspiratory feature quantity and an expiratory feature quantity of the sub-region and to calculate a value of a ratio of the calculated inspiratory feature quantity to expiratory feature quantity and which creates a histogram of the calculated ratio value; and a display unit which displays the histogram created by the analysis unit.

Advantageous Effect of the Invention

According to the present invention, the analysis results (clinical feature information) concerning ventilation in lung fields can be visually provided. This enables grasping the clinical features without depending on experiences of physicians and allows for early treatment based on early recognition of lesions.

BRIEF DESCRIPTION OF THE DRAWINGS

FIG. 8C is a view illustrating an example of a display screen that displays analysis results from the analysis for a dynamic image of lung fields in mixed disease in the first embodiment;

FIG. 17 is a diagram illustrating a display example of index values representing the tendency of "inspiratory feature quantity" or "expiratory feature quantity".

EMBODIMENT FOR CARRYING OUT THE INVENTION

Figure 1:
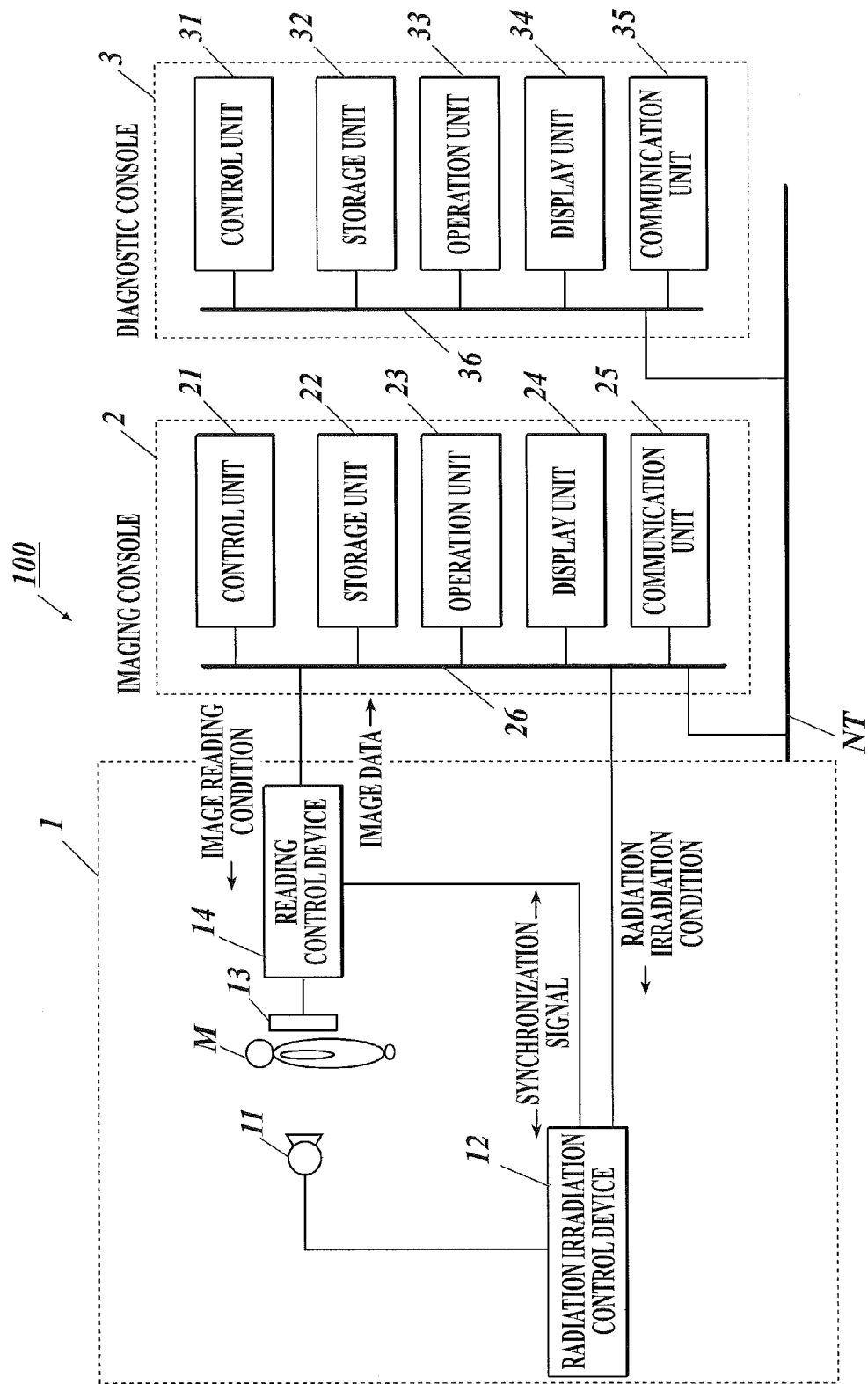
FIG. 1 is a diagram illustrating the entire configuration of a thoracic diagnosis assistance system according to a first embodiment of the present invention.

<First Embodiment> Hereinafter, a description is given of a first embodiment of the present invention in detail with reference to the drawings. The scope of the invention is not limited to the examples shown in the drawings.

[Configuration of Thoracic Diagnosis Assistance System 100]

First, a description is given of the configuration.

FIG. 1 illustrates the entire configuration of a thoracic diagnosis assistance system 100 in the present embodiment.

As shown in FIG. 1, the thoracic diagnosis assistance system 100 includes: an imaging apparatus 1, an imaging console 2, and a diagnostic console 3. The imaging apparatus 1 and imaging console 2 are connected through a communication cable or the like, and the imaging console 2 and diagnostic console 3 are connected through a communication network NT such as a LAN (local area network). Each device constituting the thoracic diagnosis assistance system 100 conforms to the DICOM (Digital Image and Communications in Medicine) standard, and the communications among the devices is performed following the DICOM standard.

[Configuration of Imaging Apparatus 1]

The imaging apparatus 1 images cyclic chest movements such as heartbeats and morphology changes between expanded and contracted lungs associated with breathing movement, for example. The dynamic imaging is performed by successively irradiating the chest portion of a human body with radiation such as X rays to acquire plurality of images (that is, successive imaging). The series of images acquired by the successive imaging is called a dynamic image. Each of the plurality of images constituting the dynamic image is called an image frame.

As shown in FIG. 1, the imaging apparatus 1 includes a radiation source 11, a radiation irradiation control device 12, a radiation detector 13, a reading control device 14, and the like.

The radiation source 11 is located in a position opposite to the radiation detector 13 with a subject M interposed therebetween and irradiates radiation (X rays) to the subject M under the control of the radiation irradiation control device 12.

The radiation irradiation control device 12 is connected to the imaging console 2 and controls the radiation source 11 based on the radiation irradiation conditions inputted from the imaging console 2 for radiation imaging. The radiation irradiation conditions inputted from the imaging console 2 include the pulse rate, pulse width, and pulse interval for successive irradiation, the number of frames imaged during one time imaging, the value of X-ray tube current, the value of X-ray tube voltage, and the filter type, for example. The pulse rate is the number of times of radiation irradiation per second and is equal to a frame rate described later. The pulse width is irradiation time of one-time radiation irradiation. The pulse interval is a period from the start of one-time radiation irradiation to the start of the next radiation irradiation in successive imaging and is equal to a frame interval later described.

The radiation detector 13 is composed of a semiconductor image sensor such as a FPD. The FPD includes a glass substrate or the like, for example, on which plurality of pixels are arranged at predetermined positions in a matrix fashion. The pixels detect radiation which is irradiated from the radiation source 11 and is transmitted through at least the subject M depending on the intensity thereof, converts the detected radiation to an electric signal, and stores the same. Each pixel is composed of a switching portion such as a TFT (Thin Film Transistor), for example.

The reading control device 14 is connected to the imaging console 2. The reading control device 14 controls the switching portion of each pixel of the radiation detector 13 based on the image reading conditions inputted from the imaging console 2 and switches reading of the electric signal stored in each pixel to read the electric signals stored in the radiation detector 13, thus acquiring image data. This image data corresponds to an image frame. The reading control device 14 outputs the acquired image frame to the imaging console 2. The image reading conditions include, for example, the frame rate, frame interval, pixel size, image size (matrix size), and the like. The frame rate is the number of image frames acquired per second and is equal to the pulse rate. The frame interval is a period from the start of an operation of acquiring an image frame to the start of the operation of acquiring the next image frame once in successive imaging and is equal to the pulse interval.

Herein, the radiation irradiation control device 12 and the reading control device 14 are connected to each other and exchange synchronization signals from each other for synchronizing the radiation irradiation operation and the image reading operation. Moreover, during calibration to acquire a plurality of dark images with which an offset correction coefficient used in later-described offset correction is calculated, the series of steps of image reading operation including resetting, storing, data reading, and resetting are performed in the absence of radiation not in synchronization with the radiation irradiation operation. The above may be performed at a timing before the series of operation of dynamic imaging or after the series of operation of dynamic imaging.

[Configuration of Imaging Console 2]

The imaging console 2 outputs the radiation irradiation conditions and image reading conditions to the imaging apparatus 1 to control the radiation imaging and radiation image reading operation by the imaging apparatus 1 and displays a dynamic image acquired by the imaging apparatus 1 with which a radiological technologist checks the positioning and determines whether the image is suitable for diagnosis.

As shown in FIG. 1, the imaging console 2 includes a control unit 21, a storage unit 22, an operation unit 23, a display unit 24, and a communication unit 25, which are connected through a bus 26.

The control unit 21 is composed of a CPU (Central Processing Unit), a RAM (Random Access Memory), and the like. In response to the operation on the operation unit 23, the CPU of the control unit 21 reads a system program and various processing programs stored in the storage unit 22 to be expanded in the RAM and executes the various processing, including a later-described imaging control processing according to the expanded programs. The CPU thus performs centralized control of the operation of each section of the imaging console 2 and the radiation irradiation operation and the reading operation of the imaging apparatus 1.

The storage unit 22 is composed of a non-volatile semiconductor memory, a hard disk, or the like. The storage unit 22 stores various programs executed by the control unit 21, parameters necessary for the programs to execute the processing, or data including processing results, etc. For example, the storage unit 22 stores an imaging control processing program to execute the imaging control processing shown in FIG. 2. Moreover, the storage unit 22 stores the radiation irradiation conditions and image reading conditions associated with each examination target portion. The various programs are stored in the form of a readable program code, and the control unit 21 sequentially executes the operation according to the program code.

The operation unit 23 is provided with a keyboard including cursor keys, numeric input keys, and various function keys and a pointing device such as a mouse. The operation unit 23 outputs to the control unit 21, instruction signals inputted by a key operation on the keyboard and a mouse operation. The operation unit 23 may include a touch panel on the display screen of the display unit 24. In this case, the operation unit 23 outputs to the control unit 21, instruction signals inputted through the touch panel.

The display unit 24 is composed of a monitor such as a LCD (Liquid Crystal Display) or a CRT (Cathode Ray Tube) and displays instructions inputted from the operation unit 23, data, and the like according to instructions of display signals inputted from the control unit 21.

The communication unit 25 includes a LAN adapter, a modem, a TA (terminal adapter), and the like and controls data exchange among the devices connected to the communication network NT.

[Configuration of Diagnostic Console 3]

The diagnostic console 3 is a moving image processing apparatus which acquires a dynamic image from the imaging console 2 and displays the acquired dynamic image and diagnosis assistance information including a later-described histogram for interpretation and diagnosis by a physician.

As shown in FIG. 1, the diagnostic console 3 includes a control unit 31, a storage unit 32, an operation unit 33, a display unit 34, and a communication unit 35, and each unit is connected through a bus 36.

The control unit 31 is composed of a CPU, a RAM, and the like. In response to operation on the operation unit 33, the CPU of the control unit 31 reads a system program and various processing programs stored in the storage unit 32 to be expanded in the RAM and executes various processing including a later-described image analysis processing according to the expanded programs. The CPU thus performs centralized control for the operation of each section of the diagnostic console 3. The control unit 31 executes the later-described image analysis processing to implement functions as an extraction unit, a region dividing unit, and an analysis unit.

The storage unit 32 is composed of a non-volatile semiconductor memory, a hard disk, or the like. The storage unit 32 stores various programs, including an image analysis processing program to execute the image analysis processing by the control unit 31, parameters necessary for the programs to execute processing, or data including processing results, etc. These various programs are stored in the form of a readable program code, and the control unit 31 sequentially executes operations according to the program code.

The operation unit 33 is provided with a keyboard including cursor keys, numeric input keys, and various function keys and a pointing device such as a mouse. The operation unit 33 outputs to the control unit 31, instruction signals inputted by a key operation on the keyboard and a mouse operation. The operation unit 33 may include a touch panel on the display screen of the display unit 34. In this case, the operation unit 33 outputs to the control unit 31, instruction signals inputted through the touch panel.

The display unit 34 is composed of a monitor such as a LCD or a CRT and displays instructions inputted from the operation unit 33, data, or the like according to instructions of display signals inputted from the control unit 31.

The communication unit 35 includes a LAN adapter, a modem, a TA, and the like and controls data exchange among the devices connected to the communication network NT.

[Operation of Thoracic Diagnosis Assistance System 100]

Next, a description is given of the operation of the thoracic diagnosis assistance system 100.

(Operation of Imaging Apparatus 1 and Imaging Console 2)

First, imaging operation by the imaging apparatus 1 and imaging console 2 is described.

Figure 2:
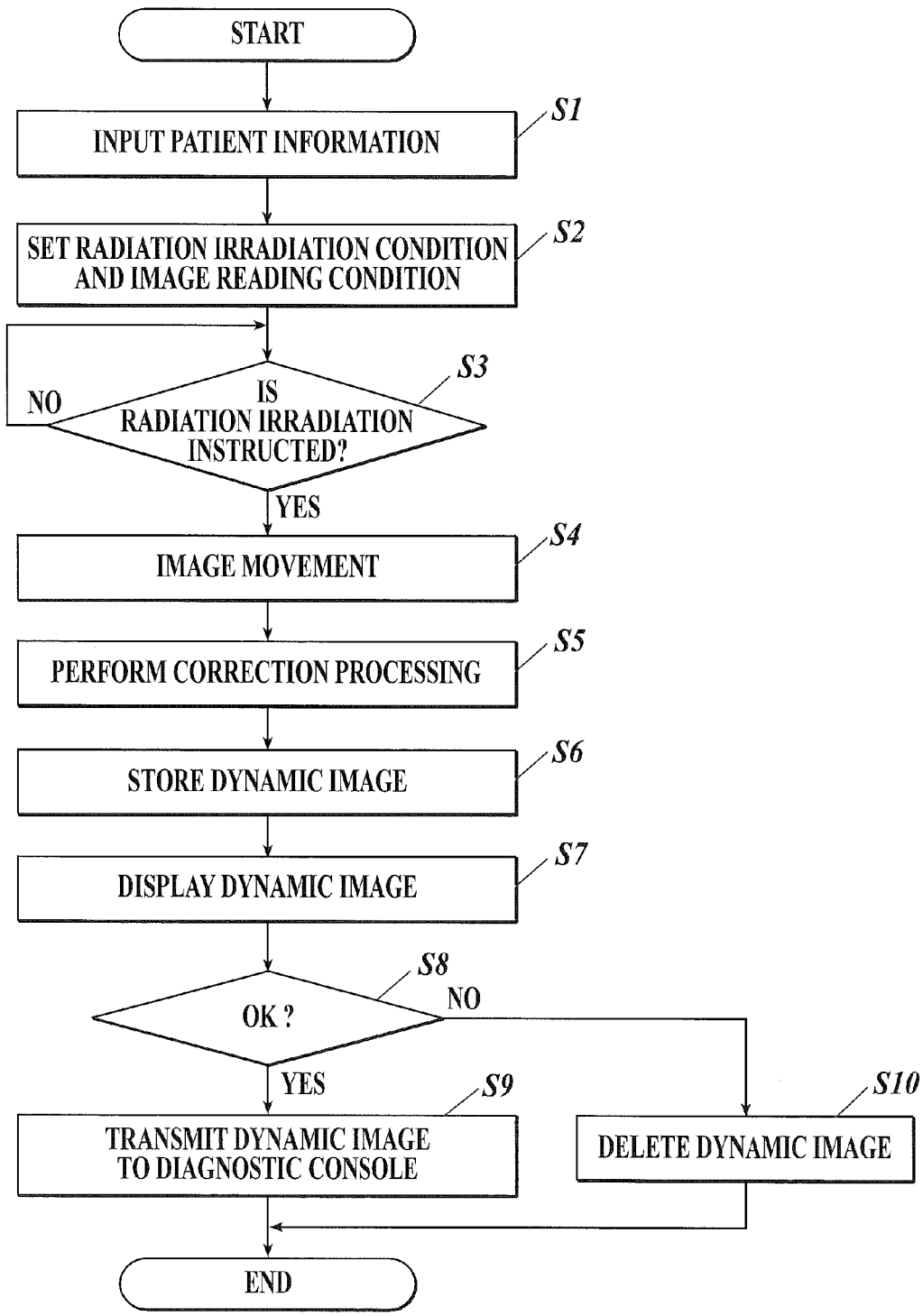
FIG. 2 is a flowchart illustrating an imaging control processing executed by a control unit of an imaging console of FIG. 1.

FIG. 2 illustrates the imaging control processing executed in the control unit 21 of the imaging console 2. The imaging control processing is executed by the control unit 21 in cooperation with an imaging control processing program stored in the storage unit 22.

At first, a radiographer operates the operation unit 23 of the imaging console 2, and inputs patient information (patient's name, height, weight, age, sex, and the like) of an imaging target (the subject M) (step S1).

Next, the radiation irradiation conditions are read from the storage unit 22 to be set in the radiation irradiation control device 12, and the image reading conditions are read from the storage unit 22 and are set in the reading control device 14 (step S2).

Next, a radiation irradiation instruction by an operation of the operation unit 23 is waited (step S3). Herein, the radiographer prepares for imaging such as positioning of the subject M with the imaging apparatus 1 and instructs the examinee (subject M) to be relaxed. The radiographer further urges resting breathing for imaging movements during resting breathing. At the time when the preparation for imaging is completed, the radiographer operates the operation unit 23 to input the radiation irradiation instruction.

When the radiation irradiation instruction is inputted on the operation unit 23 (step S3; YES), an instruction to start imaging is outputted to the radiation irradiation control device 12 and the reading control device 14 to start dynamic imaging (step S4). Specifically, radiation is irradiated from the radiation source 11 at the pulse intervals set in the radiation irradiation control device 12, and the radiation detector 13 acquires image frames. When imaging is finished for the predetermined number of frames, the control unit 21 outputs an instruction to terminate imaging to the radiation irradiation control device 12 and reading control device 14, and the imaging operation is stopped. The number of imaged frames is the number of frames to enable imaging of at least one breathing cycle.

The image frames acquired by imaging are sequentially inputted into the imaging console 2 and each image frame is subjected to a correction processing (step S5). The correction processing of step S5 includes three correction processing including offset correction processing, gain correction processing, and defective pixel correction processing. First, the offset correction processing is performed for each of the acquired image frames to remove the offset value due to dark current superposed on each acquired image frame. In the offset correction processing, for example, a previously stored offset correction coefficient is subtracted from each pixel value (a density value, referred to as a signal value hereinafter) of each acquired image frame. Herein, the offset correction coefficient is an image obtained by averaging a plurality of image frames previously acquired in the absence of radiation. The gain correction processing is then performed to remove variations in pixels due to individual differences of the detection elements corresponding to pixels of each image frame or variations in the gains of readout amplifiers. In the gain correction processing, for example, each offset-corrected image frame is multiplied by a previously stored gain correction coefficient. Herein, the gain correction coefficient is a coefficient previously calculated and stored based on the relationship between an image which is an average of the plural offset-corrected image frames acquired when the radiation detector 13 is irradiated with uniform radiation and output signal values which are expected under the radiation irradiation conditions at this time so that each pixel after the gain correction has a same signal value. Subsequently, the defective pixel correction processing is performed to remove pixels having nonlinear sensitivity compared with pixels therearound and missing pixels having no sensitivity. In the defective pixel correction processing, for example, according to a previously stored defective pixel positional information map, the signal value of each defective pixel registered in the defective pixel positional information map is replaced with an average value of signal values of nearby non-defective pixels. Herein, the defective pixel positional information map is a map registering the positions of a plurality of defective pixels previously recognized from the image frames which are obtained by uniform radiation irradiated onto the radiation detector 13 and are then subjected to the offset correction and gain correction. The offset correction coefficient and the gain correction coefficient and the defective pixel positional information have optimal values previously stored depending on the acquisition mode including binning and dynamic range, and the optimal values corresponding to each acquisition mode are read out.

Subsequently, the image frames after the correction processing and the numbers indicating the order of imaging, which are correlated to each other, are stored in the storage unit 22 (step S6) and are displayed on the display unit 24 (step S7). Herein, each image frame may be subjected to a logarithmic transformation processing which transforms the signal value of each pixel of each image frame from an antilogarithm to a logarithm just before the image frame is stored and then the image frame may be stored. The radiographer checks the positioning, etc. based on the displayed dynamic image and determines whether the image obtained by imaging is suitable for diagnosis (imaging: OK) or retaking is necessary (imaging: NG). The radiographer operates the operation unit 23 and inputs the determination result. The image frames obtained by imaging may be collectively inputted after all image frames are imaged.

If the determination result indicating that imaging is OK is inputted by a predetermined operation of the operation unit 23 (step S8: YES), additional information such as the identification ID for identifying the dynamic image, the patient information, the examination target portion, the radiation irradiation conditions, the image reading conditions, the number indicating the order of imaging, and the imaging date is attached to each of the series of image frames obtained by dynamic imaging (for example, the information is written in the header area of image data in a DICOM format). The series of image frames are then transmitted to the diagnostic console 3 through the communication unit 25 (step S9). The processing is then terminated. On the other hand, if the determination result indicating that imaging is NG is inputted by a predetermined operation of the operation unit 23 (step S8; NO), the series of image frames stored in the storage unit 22 are deleted (step S10), and the processing is terminated. In this case, retaking is to be executed.

(Operation of Diagnostic Console 3)

Next, a description is given of the operation of the diagnostic console 3.

Figure 3:
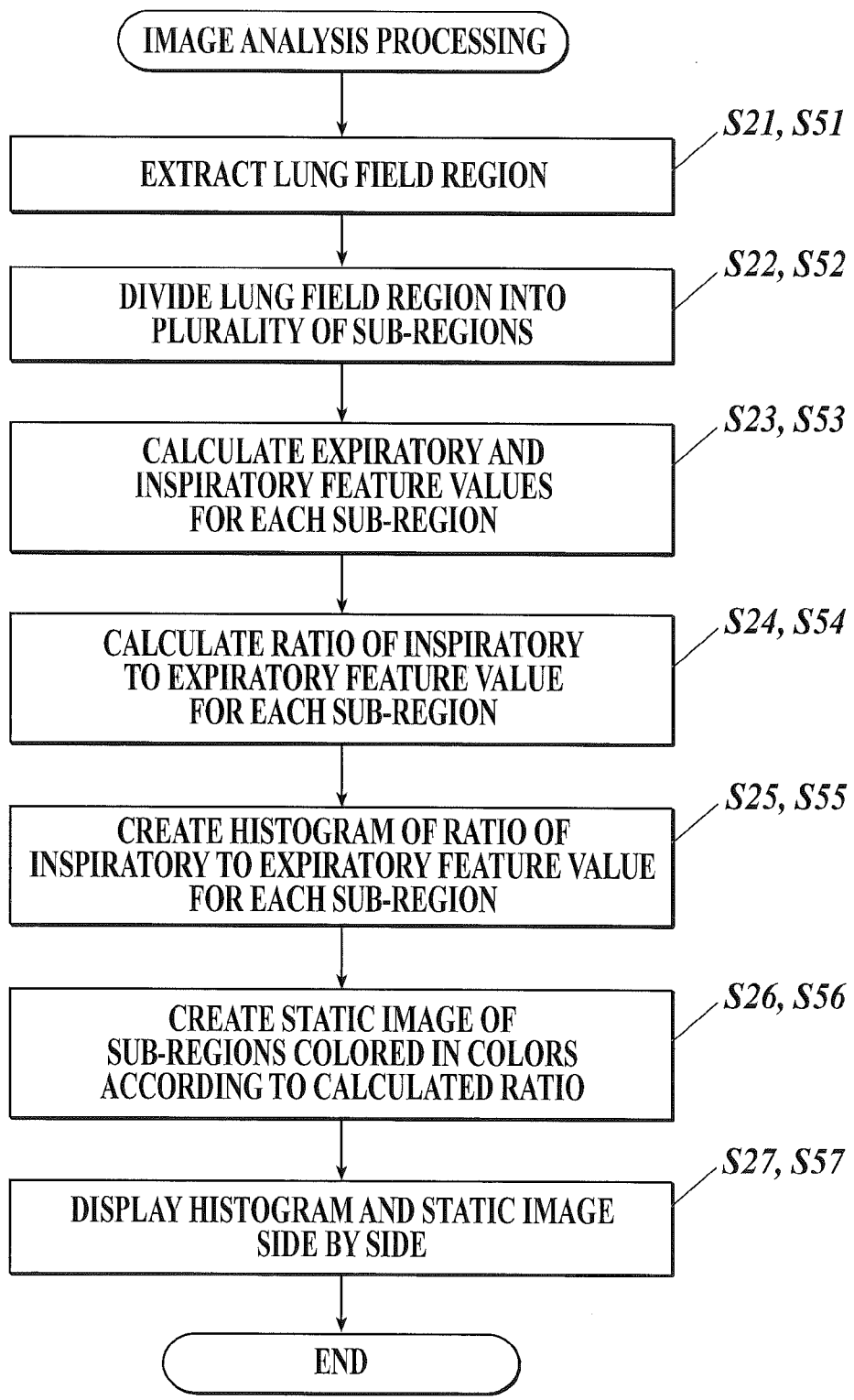
FIG. 3 is a flowchart illustrating an image analysis processing executed by a control unit of a diagnostic console of FIG. 1.

In the diagnostic console 3, when the series of image frames of the dynamic image are received from the imaging console 2 through the communication unit 35, the control unit 31 executes the image analysis processing shown in FIG. 3 in cooperation with an image analysis processing program stored in the storage unit 32.

Hereinafter, a description is given of the sequence of the image analysis processing with reference to FIG. 3.

First, lung field regions are extracted from each image frame (step S21).

The method of extracting lung field regions may be any method. For example, based on a histogram of signal values (concentration values) of pixels of any one of the image frames in the series of image frames (herein, the first (beginning) image frame in the order of imaging), a discrimination analysis is performed to calculate a threshold value, and the region having signal values higher than the calculated threshold value is primarily extracted as a lung field region candidate. Next, edge detection is performed around the boundary of the primarily extracted lung field region candidate to extract, along the boundary, the point having the maximum edge in each small region around the boundary. The boundary of the lung field region can be thus extracted.

Next, the lung field regions of each image frame are divided into plurality of sub-regions, and the sub-regions of each image frame are correlated with sub-regions of the other image frames (step S22). The positions of the pixels of the sub-regions are stored in the RAM of the control unit 31.

Figure 4:
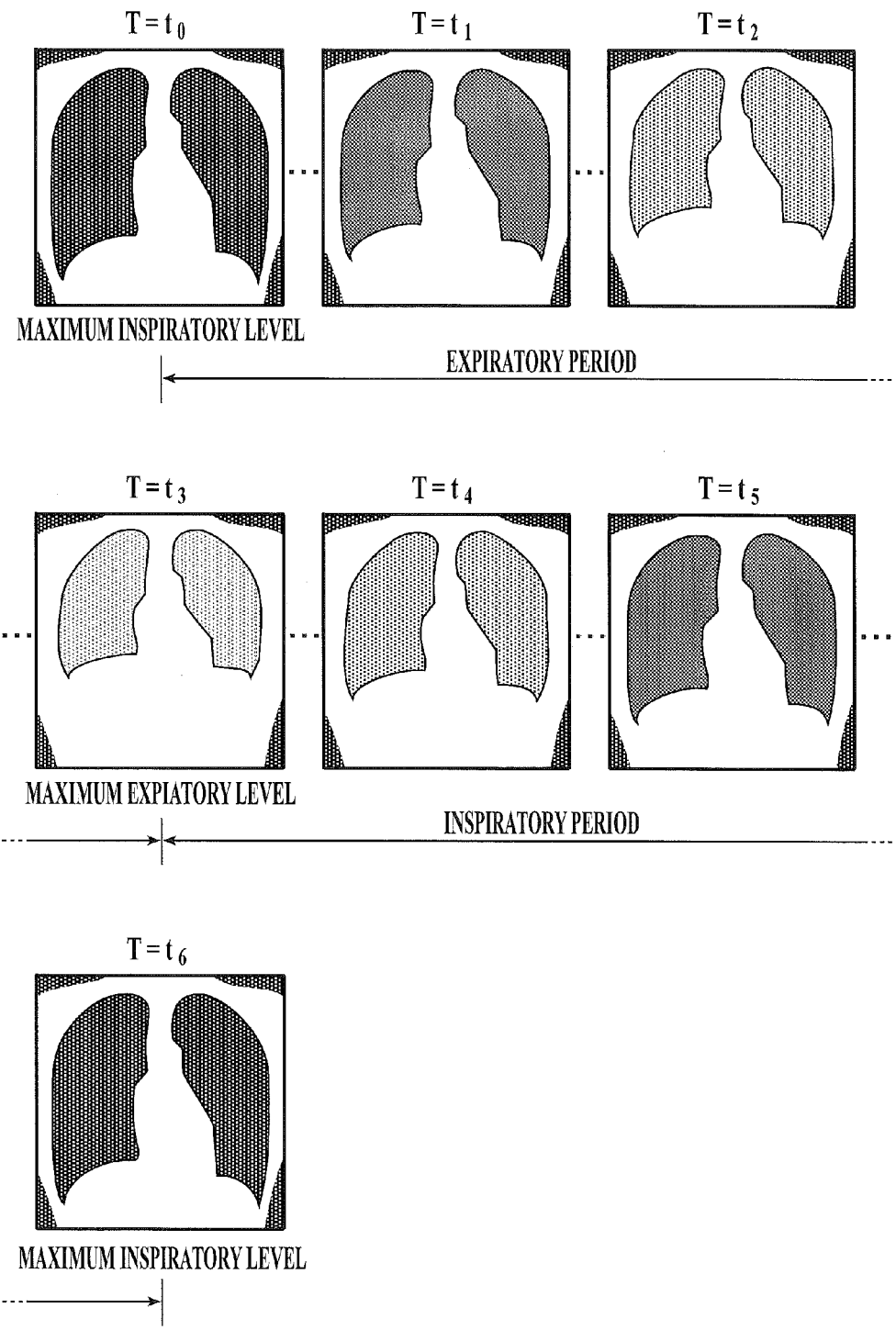
FIG. 4 is a view illustrating image frames at plurality of time phases T (T=t0 to t6) that are imaged during one breathing cycle (at deep breathing)

Herein, the breathing cycle is composed of an expiratory period and an inspiratory period. FIG. 4 is a diagram illustrating image frames at a plurality of time phases T (T=t0 to t6) imaged in one breathing cycle (in deep breathing). As shown in FIG. 4, in the expiratory period, the diaphragm moves up to discharge air from the lungs, and the lung field regions are reduced in size. At the maximum expiratory level, the position of the diaphragm is the highest. In the inspiratory period, the diaphragm moves down to take air into the lungs, so that the lung field regions in the rib cage increase in size as shown in FIG. 4. At the maximum inspiratory level, the position of the diaphragm is the lowest. In other words, the position of same part of a lung field region changes with time according to the breathing movement, and the pixel position representing same part of the lung field (especially, in lower region (near the diaphragm)) are located at different positions among the image frames.

Figure 5:
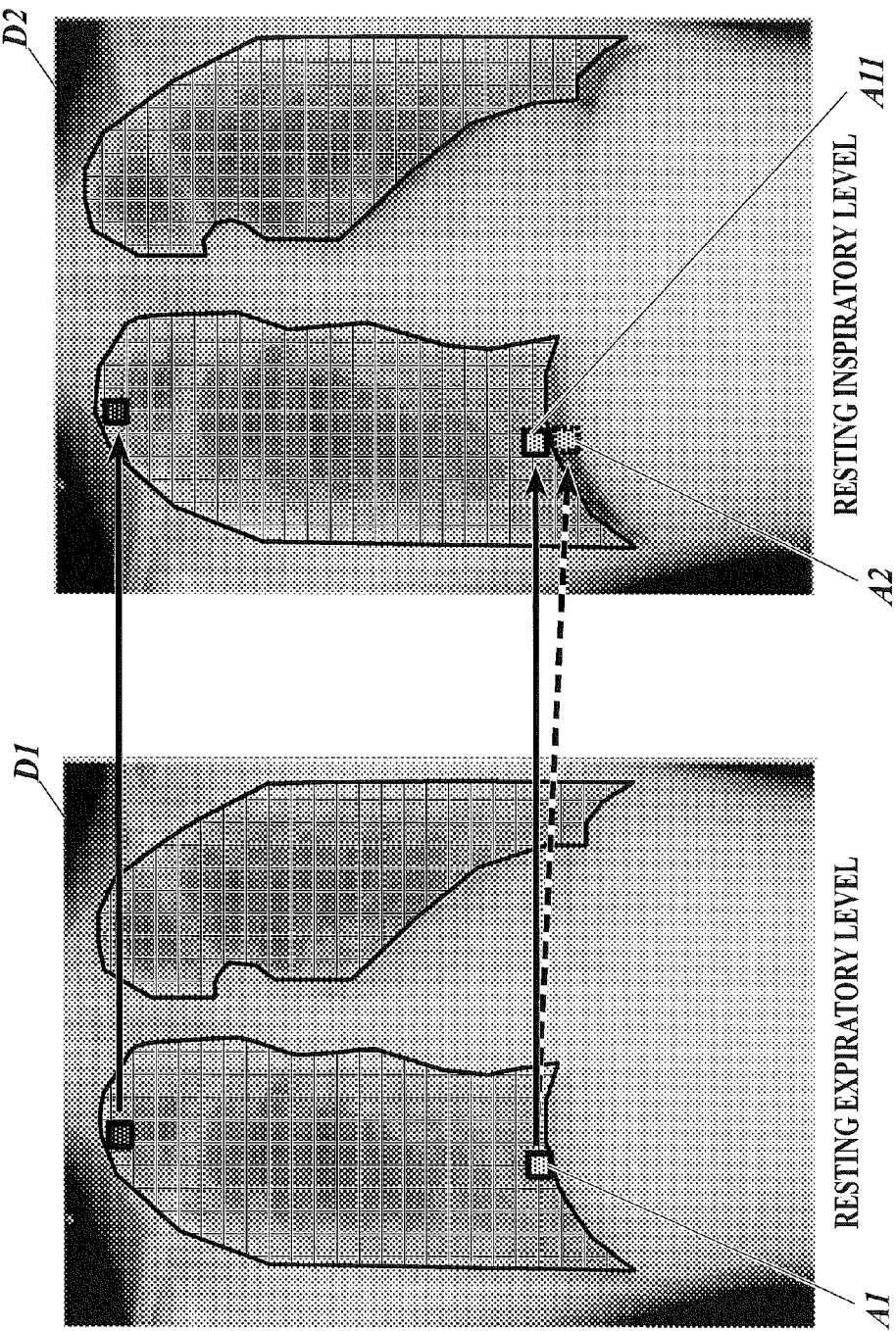
FIG. 5 is a view illustrating a difference in position between regions in which same portion of the lung field is rendered at the resting expiratory level and resting inspiratory level.

However, in images imaged during quiet breathing, the aforementioned positional differences are small and therefore positional differences large enough to confound the later described analysis results do not occur. The image D1 of FIG. 5 is an image frame at the resting expiratory level (at the time when the diaphragm is at the highest position in quiet breathing). The image D2 of FIG. 5 is an image frame at the resting inspiratory level (at the time when the diaphragm is at the lowest position during quiet breathing). In other words, the images D1 and D2 of FIG. 5 are images imaged at the timing when the difference in shape is maximized during one breathing cycle. However, it is found that the positional difference between the images D1 and D2 of FIG. 5 is very small even in the lower region of the lung field regions including the largest positional difference (All of the image D2 indicates the same pixel position as A1 of the image D1, and A2 of the image D2 indicates a region which renders the same portion of the lung field as A1 of the image D1).

Accordingly, as the concrete processing in step S22, first, one of the frame images in the series of image frames is set as a referential image. Next, the lung field regions extracted in the referential image are divided into a plurality of sub-regions (rectangular regions of 2 mm×2 mm, for example) (see FIG. 5). Subsequently, the lung field regions of another image frame are divided into sub-regions at the same pixel positions as those of the sub-regions of the referential image (regions of signal values outputted from the same image capturing elements of the radiation detection unit 13). Then, each sub-region of each image frame is correlated with sub-regions at the same pixel position among the image frames. In this processing, division and correlation of the sub-regions of each image frame can be performed at high speed.

The referential image is preferably an image frame at the resting expiratory level. At the resting expiratory level, the diaphragm is located at the highest position in quiet breathing. In other words, the area of the lung field region is minimized. Accordingly, when the sub-regions of the referential image are correlated with another image frame, the sub-regions thereof are not correlated with regions outside of the lung field in the other image frame.

Figure 6:
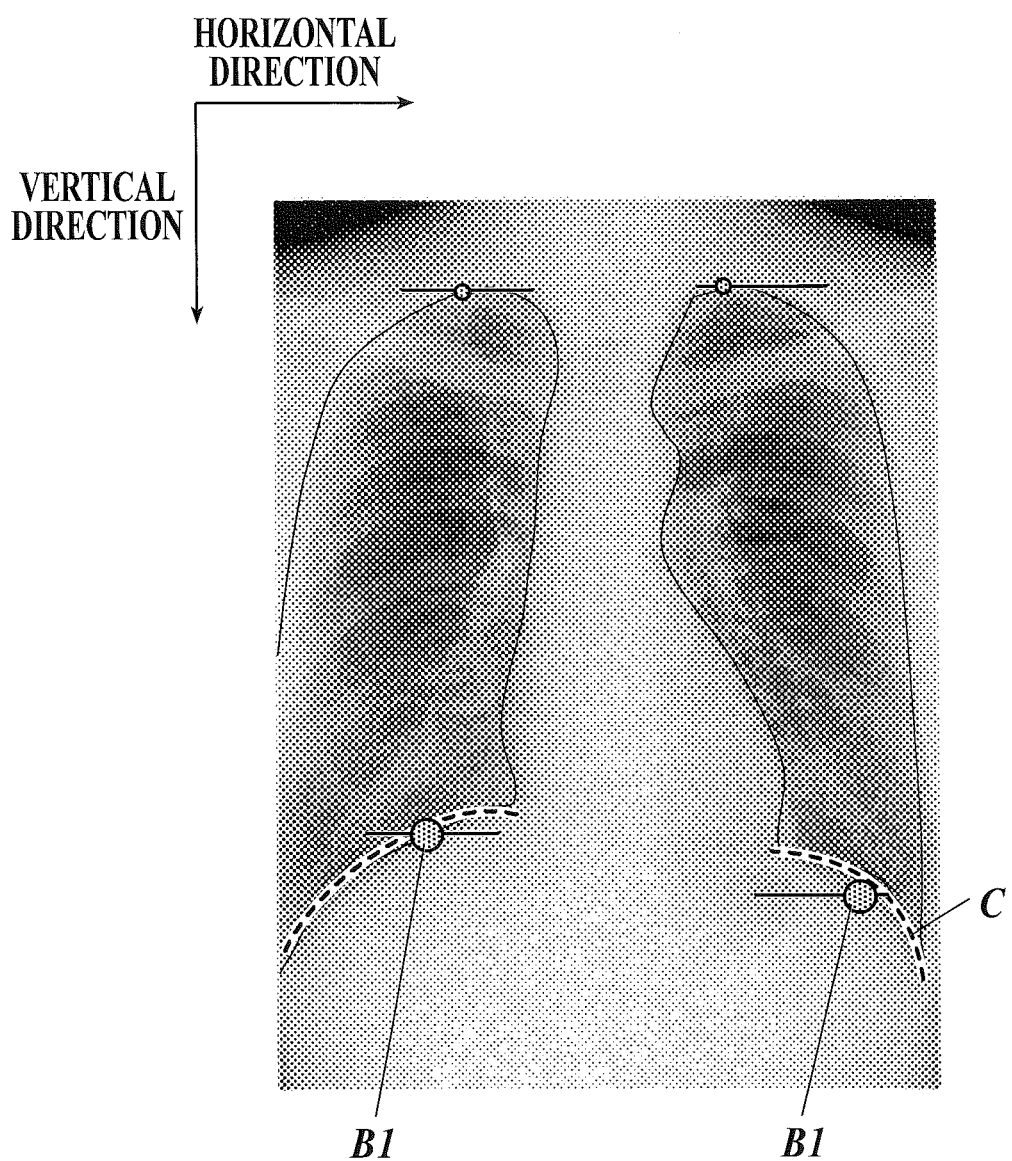
FIG. 6 is a view for explaining a method of calculating the position of the diaphragm.

The image at the resting expiratory level can be obtained by extracting an image in which the diaphragm is located at the highest position in the series of image frames. As for the position of the diaphragm, for example, referential positions B1 of the diaphragm shown in FIG. 6 are previously defined as average positions of curves C of the diaphragm in the vertical direction (as indicated by dashed lines in FIG. 6). The curves C of the diaphragm (the lower ends of the lung field regions) are extracted from lung field regions R, and the average positions in the vertical direction are calculated. The calculated positions are specified as the referential positions B1 of the diaphragm.

Figure 7:
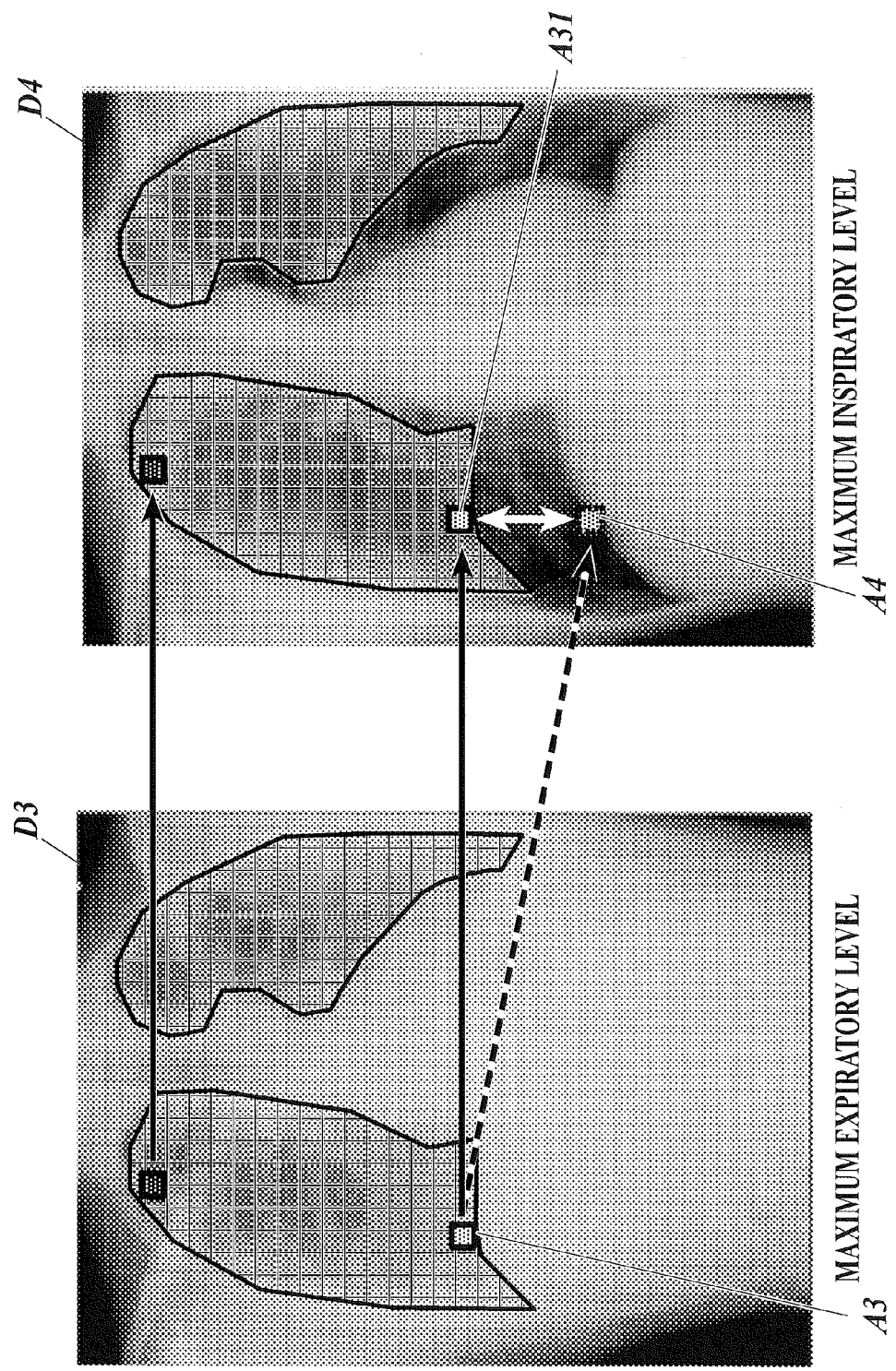
FIG. 7 is a view illustrating a change in position between regions in which same portion of the lung field is rendered at the maximum expiratory level and maximum inspiratory level.

When the dynamic image is an image imaged during deep breathing, as shown in FIG. 7, the pixel positions indicating the same portion of the lung fields are greatly different from each other. Herein, an image D3 of FIG. 7 is an image frame at the maximum expiratory level during deep breathing, and an image D4 of FIG. 7 is an image frame at the maximum inspiratory level during deep breathing (A31 of the image D4 indicates the same pixel position as A3 of the image D3, and A4 of the image D4 indicates a region which renders the same portion of the lung field as A3 of the image D3). Accordingly, if the regions at the same pixel positions in each image frame as the sub-regions of the referential image are defined as the regions corresponding to the sub-regions in a similar manner to the case of quiet breathing, the later-described analysis result cannot be utilized in diagnosis. In such a case, a corresponding point extraction processing which extracts corresponding points in different image frames (local matching processing) and a nonlinear distortion conversion processing (warping processing) are performed to correlate the regions rendering the same portion of the lung field regions in the image frames to each other. In order to further increase the analysis accuracy without placing value on the processing speed, the processing may be used for the case of quiet breathing.

In the local matching processing, first, each lung field region extracted from the image frame which is the first (beginning) in the order of imaging is divided into sub-regions of 2 mm rectangles.

Herein, the first image frame in the order of imaging is indicated by P1, and the image frame adjacent thereto (the adjacent image frame in the order of imaging (that is, the image frame chronologically adjacent to the first image frame. The same hereinafter)) is indicated by P2. In the image frame P1, a search region is set for each sub-region of P1. Herein, the search region of P2 is set so as to have a central point (x, y) the same as the coordinates (x, y) of the central point in the corresponding sub-region of P1 and have vertical and horizontal widths larger than those of the sub-regions of P1 (for example, 1.5 times). Then, for each region of P1, a region in the search range of P2 that has the highest matching degree with the same is obtained to calculate the corresponding positions on P2 with respect to each sub-region of P1. As the matching degree, the least square technique or cross correlation coefficient is used as the index. The lung field regions of P2 are divided at the positions corresponding to the sub-regions of P1.

Subsequently, P2 is newly set to P1, and the image frame next to P2 in the order of imaging is newly set to P2. The position in P2 corresponding to each sub-region of P1 is calculated. The aforementioned processing is repeated to obtain which position each sub-region of each image frame corresponds to in the adjacent image frame. The calculated processing result is stored in the RAM of the control unit 31.

Subsequently, the warping processing is performed. Specifically, where the first image frame in the order of imaging is P1 and the image frame adjacent thereto in the order of imaging (chronologically adjacent thereto) is P2, based on the corresponding positions of each sub-region in the image frames adjacent to each other, which are calculated by the local matching processing, a shift vector from P1 to P2 is calculated for each sub-region. Next, fitting with a polynomial is performed for the calculated shift vector, and the polynomial is used to calculate the shift vector of each pixel in each sub-region. Based on the calculated shift vector of each pixel, the warping processing is performed to shift the position of each pixel in each sub-region of P2 to the position of the corresponding pixel of the image frame P1. Subsequently, the P2 subjected to the warping processing is newly set as P1, and the image frame next to P2 in the order of imaging is set as new P2 for execution of the above processing. When the aforementioned processing is sequentially repeated starting from the adjacent image frames in the earlier order of imaging, the positions of the sub-regions in each image frame can be substantially coincident with those of the first image frame in the order of imaging (the referential image in this processing). The corresponding relationship of the positions of the sub-regions among the image frames is stored in the RAM of the control unit 31.

Next, the analysis is performed for the sub-regions correlated with each other in step S22 in the series of image frames to calculate inspiratory feature quantities and expiratory feature quantities (step S23). Herein, as the inspiratory feature quantities and the expiratory feature quantities, for example, representative values (maximum absolute values) of inter-frame difference values (differential values) of each sub-region during the inspiratory period and the expiratory periods are calculated. The inter-frame difference values are values representing signal changing amounts at the timing when the image frame of interest is imaged. In breathing to inhale and exhale air, the density in the lungs changes with the flow of breath, and the amount of transmitted X-ray (that is, signal values outputted from pixels) changes. The signal changing amounts can be considered as values representing the airflow rate at the timing. The representative values are not limited to the absolute maximum value but also may be center values, average values, or mode values.

Specifically, first, the signal values (average signal values) of pixels of each sub-region in each image frame are calculated. Subsequently, the inter-frame difference processing is performed to calculate the differences between the signal values of the sub-regions in the image frames adjacent to each other in the order of imaging. In this processing, a difference value (N+1–N) of the image frames of frame numbers N and N+1 (N is 1, 2, 3, . . . ) is calculated for each sub-region. The maximum value (the maximum absolute value) of the inter-frame difference values in the expiratory period is acquired as the expiratory feature quantity, and the maximum value (the maximum absolute values) of the inter-frame difference values in the inspiratory period is acquired as the inspiratory feature quantity. The maximum value (the maximum absolute value) of the inter-frame difference values is equivalent to the maximum differential value. Herein, the inspiratory period is when the sign of the inter-frame difference value in each sub-region is positive and the expiratory period is when the sign of the inter-frame difference value in each sub-region is negative.

Next, the value of the ratio of the inspiratory feature quantity to the expiratory feature quantity (inspiratory feature quantity/expiratory feature quantity) is calculated for each sub-region (step S24). In this processing, "maximum value of inter-frame difference value in the inspiratory period/maximum value of inter-frame difference value in the expiratory period" is calculated.

Next, a histogram of the values of the "inspiratory feature quantity/expiratory feature quantity" calculated for each sub-region is created. Moreover, the index values (herein, average values, standard deviations) representing the tendency of the "inspiratory feature quantity/expiratory feature quantity" in the entire lung field are calculated (step S25). In the histogram, it is preferable that the number of counts in the axis of ordinate is divided by the number of all the sub-regions in the lung fields for normalization.

Next, the values of the "inspiratory feature quantity/expiratory feature quantity" calculated for the sub-regions are converted to display parameter values based on a conversion table of values of "inspiratory feature quantity/expiratory feature quantity" and parameter values of display, which is stored in the storage unit 32 in advance. Based on the converted parameter values, an image to display each sub-region of the referential image (the image frame at the resting expiratory level, for example) is created (step S26). The conversion table is a table correlating threshold values which are used to classify feature quantities with normal/abnormal categories (severities 1 to n) (the threshold value for each category) and to specify the range of feature quantity magnitude of each category to any of hues, intensities, luminances, and transparencies one to one. Herein, the conversion table of display parameter values preferably correlates the threshold value of each category with a hue in order to enhance discrimination of the magnitude of feature quantities.

At this time, for example, the threshold values of the categories are correlated with several hues (five or six hues, for example), and the values of the feature quantity between the thresholds are related to intermediate hues (the hues are gradated), thus implementing display providing high quality in ability of discrimination.

The image colored based on the display parameter values may be displayed overlaid on the image frame set as the referential image.

The created histogram, the created static image, and the like are displayed side by side on the display unit 34 (step S27), and the image analysis processing is terminated. The region of the histogram is displayed colored based on the same criteria as the sub-regions of the lung field regions of the referential image according to the aforementioned conversion table of values of the "inspiratory feature quantity/expiratory feature quantity" and parameter values of display.

Figure 8A:
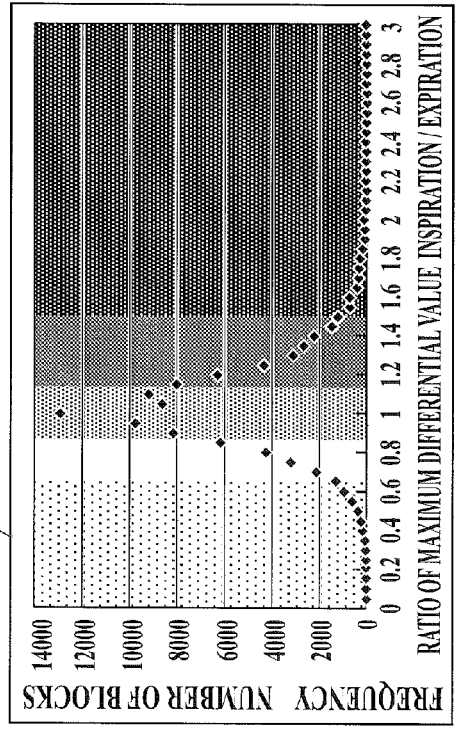
FIG. 8A is a view illustrating an example of a display screen that displays analysis results from the analysis for a dynamic image of lung fields of a normal subject in the first embodiment.
Figure 8B:
FIG. 8B is a view illustrating an example of a display screen that displays analysis results from the analysis for a dynamic image of lung fields in COPD (chronic obstructive pulmonary disease) in the first embodiment.

FIG. 8A to FIG. 8C illustrate examples of the display screen displayed on the display unit 34 in step S27.

FIG. 8A is a display screen displaying the analysis results from the analysis for a dynamic image of lung fields of a normal subject. FIG. 8B is a display screen displaying the analysis result from the analysis for a dynamic image of lung fields in COPD (obstructive disease). FIG. 8C is a display screen displaying the analysis result from the analysis for a dynamic image of lung fields in mixed disease.

As shown in FIG. 8A to FIG. 8C, in step S27, a histogram 34*a*, a static image 34*b*, a display 34*c*, and an index value 34*d* are displayed. The histogram 34*a* is a histogram of the values of the "inspiratory feature quantity/expiratory feature quantity" of the sub-regions (2 mm rectangular size) in the lung field regions extracted from an image frame of half size. The static image 34*b* displays in a list the "inspiratory feature quantity/expiratory feature quantity" of the sub-regions. The display 34*c* shows the relationship between the hues displayed in the histogram 34*a* and the static image 34*b* and values of the "inspiratory feature quantity/expiratory feature quantity". The index value 34*d* represents the tendency of the "inspiratory feature quantity/expiratory feature quantity" in the entire lung fields. Therefore, the characteristics of the distribution of the "inspiratory feature quantity/expiratory feature quantity" can be grasped. As shown in FIG. 8A to FIG. 8C, in the histogram 34*a*, the region of the axis of abscissa is displayed divided by color in five hues depending on the magnitude of the value of "inspiratory feature quantity/expiratory feature quantity". Accordingly, physicians can easily grasp the distribution of the "inspiratory feature quantity/expiratory feature quantity" in the lung fields at a glance of the histogram. In the static image 34*b* showing the "inspiratory feature quantity/expiratory feature quantity" of each sub-region, the sub-regions are displayed divided by color based on the same criteria as those of the histogram depending on the values of the "inspiratory feature quantity/expiratory feature quantity". Accordingly, physicians can easily grasp locally abnormal portion (obstructive portion or restrictive portion) in the lung fields. Furthermore, as the index value 34*d* representing the tendency of the "inspiratory feature quantity/expiratory feature quantity" in the entire lung fields, the average value and standard deviation thereof are calculated and displayed together on the screen. This can provide physicians with the tendency of the "inspiratory feature quantity/expiratory feature quantity" in the entire lung fields as numeric values.

Herein, when the maximum value (absolute value) of the inter-frame difference values in the expiratory period is set as the expiratory feature quantity, and the maximum value (absolute value) of the inter-frame difference values in the inspiratory period is set as the inspiratory feature quantity, it is known that, in lung fields of a normal subject, the average value of the "inspiratory feature quantity/expiratory feature quantity" of the entire lung field is 0.9 to 1.2, and the standard deviation thereof is about 0.10 to 0.22. Accordingly, if the display screen shown in FIG. 8A is displayed in step S27, physicians can easily grasp that the imaged lung fields are normal.

On the other hand, it is known that in lung fields in COPD (obstructive disease), the average value of the "inspiratory feature quantity/expiratory feature quantity" of the entire lung field is out of the range of 0.9 to 1.2 (larger than that of the normal subject) and the standard deviation thereof is out of the range of 0.10 to 0.22 (larger than that of the normal subject). Accordingly, if the display screen shown in FIG. 8B is displayed in step S27, physicians can easily grasp that the imaged lung fields are in COPD.

Furthermore, it is known that in lung fields in mixed lung disease, the number of pieces of data having values of the "inspiratory feature quantity/expiratory feature quantity" of the entire lung field which is not more than 0.66 and the number of pieces of data having values of the "inspiratory feature quantity/expiratory feature quantity" of the entire lung field which is not less than 1.5 are increased. Accordingly, if the display screen shown in FIG. 8C is displayed in step S27, physicians can easily grasp that the imaged lung fields are in mixed disease.

In such a manner, the thoracic diagnosis assistance system 100 is capable of providing physicians with useful diagnostic information which can specify the clinical condition such as COPD (obstructive lung disease), mixed lung disease and the like.

The feature quantity other than the aforementioned examples may be used as the expiratory feature quantity and the inspiratory feature quantity.

For example, the expiratory feature quantity may be the number of image frames corresponding to the expiratory period in one breathing cycle (expiratory time), and the inspiratory feature quantity may be the number of image frames corresponding to the inspiratory period in one breathing cycle (inspiratory time). Herein, if the ventilation function of lungs are normal, the expiratory time should be substantially equal to the inspiratory time or the expiratory time should be a little longer than the inspiratory time. Accordingly, by checking values of the "number of image frames corresponding to the expiratory period/number of image frames corresponding to the inspiratory period", physicians can understand whether the lungs are suspected to have disease. Especially, it is found that the region with the "number of image frames of the expiratory period/number of image frames of the inspiratory period" >1.5 is an obstructive portion in which ventilation through expiration is difficult to cause a delay in exhaling the taken air. The relationship of the "maximum value of inter-frame difference value in the inspiratory period/maximum value of inter-frame difference value in the expiratory period"≈expiratory time (the number of image frames of the expiratory period)/inspiratory time (the number of image frames of the inspiratory period) is satisfied. Accordingly, physicians can distinguish normal condition, COPD (obstructive lung disease), and mixed lung disease according to the judgment criteria similar to the case where the expiratory feature quantity is the maximum value of the inter-frame difference value of the expiratory period and the inspiratory feature quantity is the maximum value of the inter-frame difference value of the inspiratory period.

Alternatively, in each of the image frames of one breathing cycle, signal values (average signal values) of pixels of each sub-region are calculated, and the minimum value and the maximum value of the signal values of each sub-region in one breathing cycle are calculated. The calculated minimum value may be used as the expiratory feature quantity of the region and the maximum value may be used as the inspiratory feature quantity. It can be thought that the difference between the maximum value and the minimum value of the signal value is large in normal portion and the difference is very small in abnormal portion. This is because movement of pulmonary alveoli in the abnormal portion becomes stiff and the change in density of pulmonary alveoli becomes small. Accordingly, the physician refers to the histogram of the "maximum value of the signal value/minimum value of the signal value" and checks the average value and standard deviation thereof to determine whether the lung fields are normal or diseased. For example, if the average value of the "maximum value of the signal value/minimum value of the signal value" of the entire lung fields is more than 1 and the standard deviation thereof is small, it can be determined that the lungs function normally. On the other hand, if the average value of the "maximum value of the signal value/minimum value of the signal value" of the entire lung fields is a value close to 1 and the standard deviation is large, it can be judged that the lungs suffer from a functional disorder.

Furthermore, in addition to the average value and standard deviation, the index value representing the tendency of the "inspiratory feature quantity/expiratory feature quantity" may be the value of the "inspiratory feature quantity/expiratory feature quantity" at the peak of the number of counts (the number of blocks (sub-regions)) in the histogram or the number of counts (the number of blocks) at the peak or the ratio of the number of counts when the value of the "inspiratory feature quantity/expiratory feature quantity" is not less than a predetermined value to the number of counts when the value of the "inspiratory feature quantity/expiratory feature quantity" is not more than a predetermined value. Alternatively, these plurality of index values may be combined to create a new index value. Moreover, the "inspiratory feature quantity/expiratory feature quantity" may be converted to logarithms, and the converted logarithms may be used to create the histogram, calculate the index values, and create an image colored based on the conversion table to the display parameters.

As described above, according to the diagnostic console 3 of a thoracic diagnosis assistance system 100, the control unit 31 extracts the lung field regions from each of plurality of image frames obtained by imaging the chest movement, divides the extracted lung field region into plurality of sub-regions, and correlates the sub-regions of each image frame with the sub-regions of the other image frames. Subsequently, the control unit 31 performs an analysis for the sub-regions correlated in the plurality of image frames to calculate the inspiratory feature quantity and the expiratory feature quantity of each sub-region and calculates the value of the ratio between the calculated inspiratory feature quantity and the expiratory feature quantity, thus creating the histogram of the calculated value of the ratio. The control unit 31 then displays the created histogram on the display unit 34.

It is therefore possible to provide the physician with a histogram which is the information useful for diagnosis and represents how the ratio of the inspiratory feature quantity and the expiratory feature quantity is distributed in the lung fields. Accordingly, the physician can easily understand the clinical condition concerning the ventilation of the lung fields.

As the inspiratory feature quantity, the maximum value of the absolute value of the inter-frame difference value of the image frames chronologically next to each other in the group of image frames corresponding to the inspiratory period is calculated, and as the expiratory feature quantity, the maximum value of the absolute value of the inter-frame difference value of the image frames chronologically next to each other in the group of image frames corresponding to the expiratory period is calculated. The distribution of the ratio between the calculated inspiratory feature quantity and the expiratory feature quantity is displayed as a histogram. It is therefore possible to provide useful information for physicians to determine whether the imaged lung fields are normal or have obstructive disease or mixed disease.

As the inspiratory feature quantity, the number of image frames corresponding to the inspiratory period in one breathing cycle is calculated, and as the expiratory feature quantity, the number of image frames corresponding to the expiratory period in one breathing cycle is calculated. The distribution of the ratio between the calculated inspiratory feature quantity and the expiratory feature quantity is displayed as a histogram. It is therefore possible to provide useful information for physicians to determine whether the imaged lung fields are normal or have obstructive disease or mixed disease.

As the inspiratory feature quantity the maximum value of the pixel signal values in the plurality of image frames in one breathing cycle is calculated, and as the expiratory feature quantity, the minimum value of the pixel signal values in the plurality of image frames in one breathing cycle is calculated, and the distribution of the ratio between the calculated inspiratory feature quantity and the expiratory feature quantity is displayed as a histogram. Accordingly, it is possible to provide useful information for physicians to determine whether the imaged lung fields are normal or abnormal.

In the process of dividing the lung field regions of the plurality of image frames into sub-regions, the lung field regions of one of the image frames among the plurality of image frames is divided into plurality of sub-regions, and the lung field regions of each of the other image frames is divided into sub-regions located at the same pixel positions as the sub-regions of the one image frame. The sub-regions at the same pixel positions in the plurality of image frames are correlated. Accordingly, the division of the lung fields of each image frame into sub-regions and the correlation of the sub-regions of the image frames can be performed at high speed. As a result, it is possible to speed up the analysis process.

In the process of dividing the lung field regions of the plurality of image frames into sub-regions, the lung field regions of one image frame of the plurality of image frames is divided into plurality of sub-regions, and in each of the other image frames, regions having a high matching degree with the sub-regions of the one image frame are extracted. The lung field regions of each of the other image frames is divided into the extracted regions, and the sub-regions having high matching degree with each other in the plurality of image frames are correlated. This enables highly accurate analyses.

<Second Embodiment>

Hereinafter, a description is given of a second embodiment of the present invention in detail with reference to the drawings. The scope of the invention is not limited to the examples shown in the drawings.

Herein, in conventional radiation imaging of static images of chest portions, imaging is performed using an anti-scattered grid (hereinafter, referred to as a grid) for removing scattered radiation as described in Japanese Patent Laid-open Publication No. H10-98587 (Publicly-known Literature 1), for example.

In recent years, as described in Japanese Patent laid-open Publication No. 2005-312775 (Publicly-known Literature 2), a system is proposed which uses a radiation detector such as a FPD (flat panel detector) to image the chest movements and applies the image to diagnosis. Also in such a dynamic imaging system, imaging is performed using a grid in a similar manner to static imaging.

In Publicly-known Literature 2, in order to reduce the exposure dose of a subject during dynamic imaging in which the subject tends to be exposed to high dose of radiation, the radiation dose per image frame at dynamic imaging is calculated so that the total radiation dose concerning a series of dynamic imaging operations is substantially equal to the radiation dose of one-time static imaging. Herein, if the grid is used according to the conventional method, the dose reaching the radiation detector (detector) is attenuated. Accordingly, in dynamic imaging under the radiation irradiation conditions as described in Publicly-known Literature 2, the dose reaching each image frame is considerably insufficient, resulting in a lower S/N ratio. When the series of image frames are used to perform a movement analysis, the analysis is not accurate, requiring a change in radiation dose for reimaging. This could increase the total exposure dose of the subject.

As a result of hard studies by the inventor and the like, it is found that, unlike the static imaging for observing absolute output signals (density signals) of the detector, in the dynamic imaging, the relative output signal difference (density difference) between the frames is visually checked or the feature quantities are analyzed based on the relative output signal difference such as the inter-frame difference value. Accordingly, the object of dynamic imaging can be achieved even if substantially uniform influence of scattered radiation is superposed on each image frame.

Accordingly, dynamic imaging can be performed without a grid. In the dynamic imaging without a grid, in the case of keeping the dose reaching the detector at the level of conventional imaging, it is not necessary to previously add the dose attenuated by the grid to the radiation dose for a subject. The exposure dose of the subject can be reduced to half of that of the conventional method. Moreover, if the exposure dose (radiation dose) for the subject is kept constant, the dose reaching the detector per image frame can be increased, thus implementing highly accurate analyses.

In the second embodiment, a description is given of a radiation imaging system 200 that performs imaging without a grid at dynamic imaging.

[Configuration of Radiation Imaging System 200]

First, the configuration is described.

Figure 9:
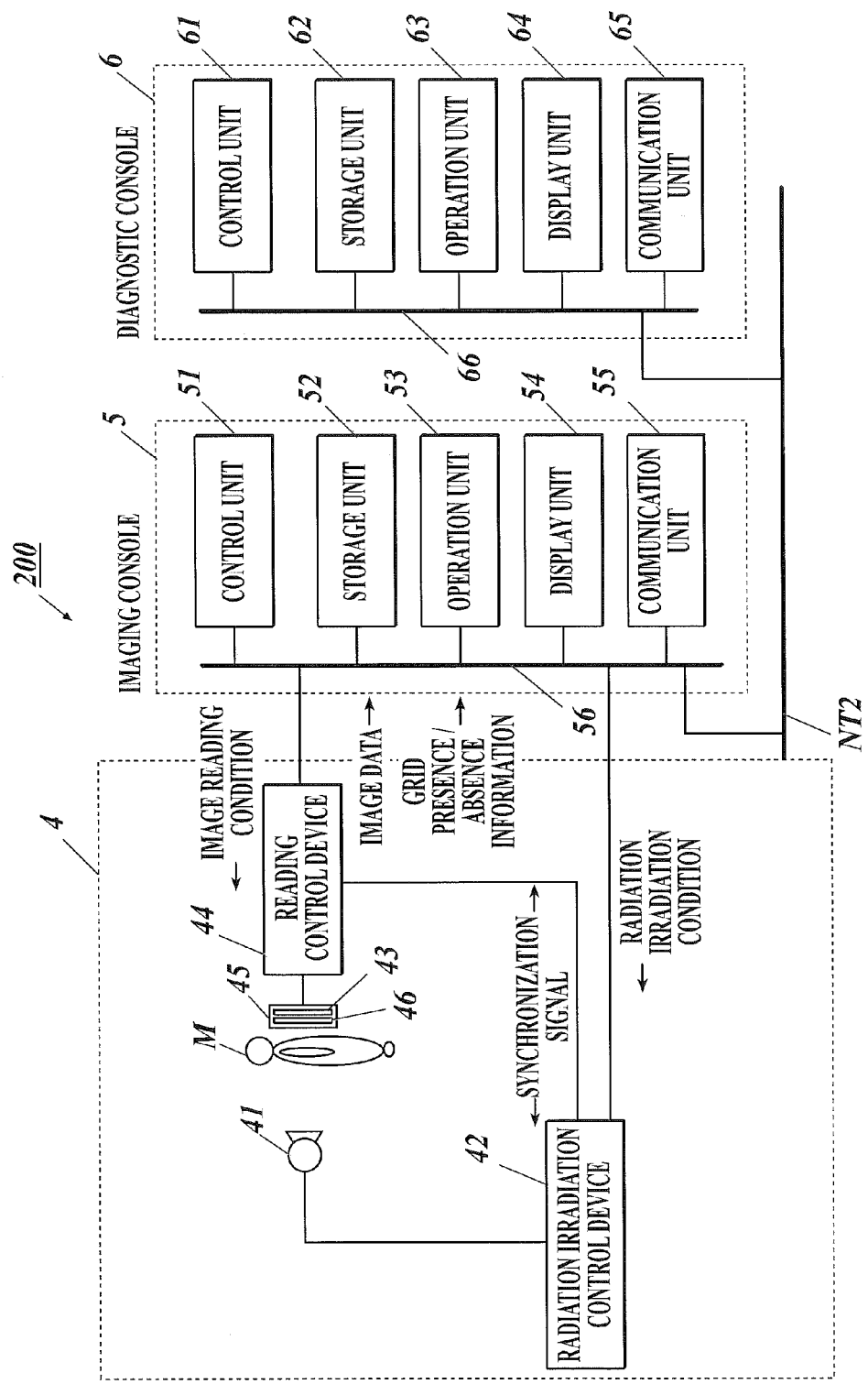
FIG. 9 is a diagram illustrating the entire configuration of a radiation imaging system according to a second embodiment of the present invention.

FIG. 9 illustrates the entire configuration of the radiation imaging system 200 of the present embodiment. The radiation imaging system 200 is a system functioning as a thoracic diagnosis assistance system.

As shown in FIG. 9, the radiation imaging system 200 includes: an imaging apparatus 4, an imaging console 5, and a diagnostic console 6. The imaging apparatus 4 and the imaging console 5 are connected through a communication cable or the like, and the imaging console 5 and the diagnostic console 6 are connected through a communication network NT2 such as a LAN (Local Area Network). Each device constituting the radiation imaging system 200 conforms to the DICOM (Digital Image and Communications in Medicine) standard, and the communications among the devices is performed following the DICOM standard.

[Configuration of Imaging Apparatus 4]

The imaging apparatus 4 is an apparatus which irradiates radiation to a subject M (the chest of a human body) for dynamic imaging or static imaging of the subject M.

The dynamic imaging refers to irradiating the subject M with successive pulses of radiation such as X-rays to acquire a plurality of images (successive imaging). By the dynamic imaging, for example, cyclic movements in the subject M are imaged, including morphology changes between expansion and contraction of the lungs accompanied with the breathing movement, heartbeats, and the like. The series of images acquired by the successive imaging is called a dynamic image. The plurality of images constituting the dynamic image are called image frames.

The static imaging is used for diagnosis based on the density resolution of the imaged site similar to a conventional film method and CR method and refers to irradiating radiation such as X-rays to the subject M once to acquire one static image.

As shown in FIG. 9, the imaging apparatus 4 includes a radiation source 41, a radiation irradiation control device 42, a radiation detector 43, a reading control device 44, a holder 45, and a grid 46.

The radiation source 41 is a radiation generator capable of performing single irradiation and successive irradiation (pulse irradiation). In other words, the radiation source 41 is a radiation generator suitable for both the static imaging and dynamic imaging. The radiation source 41 is located opposite to the radiation detector 43 with the subject M interposed therebetween and irradiates radiation (X-rays) to the subject M under the control of the radiation irradiation control device 42.

The radiation irradiation control device 42 is connected to the imaging console 5 and controls the radiation source 41 based on the radiation irradiation conditions inputted from the imaging console 5 for radiation imaging. The radiation irradiation conditions inputted from the imaging console 5 include the pulse rate, pulse width, and pulse interval at successive irradiation, the number of frames imaged during one time imaging, the value of X-ray tube current, the value of X-ray tube voltage, and the filter type, for example. The pulse rate is the number of times of radiation irradiation per second and is equal to the frame rate described later. The pulse width is irradiation time of one-time radiation irradiation. The pulse interval is a period from the start of one-time radiation irradiation to the start of the next radiation irradiation in successive imaging and is equal to a frame interval later described.

The radiation detector 43 is composed of a FPD supporting both the dynamic imaging and static imaging. The FPD includes a glass substrate or the like, for example, on which plurality of pixels are arranged at predetermined positions in a matrix fashion. The pixels detect radiation which is irradiated from the radiation source 41 and is transmitted through at least the subject M depending on the intensity thereof, converts the detected radiation to electric signal, and stores the same. Each pixel is composed of a switching portion such as a TFT (Thin Film Transistor), for example.

Figure 10:
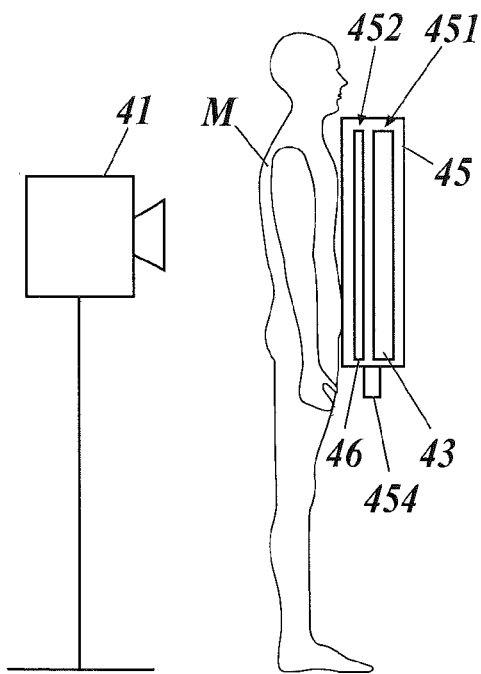
FIG. 10 is an enlarged view illustrating around a holder 45 of FIG. 9.

The radiation detector 43 is held by the holder 45 opposite of the radiation source 41 with the subject M interposed therebetween as shown in FIG. 10.

The reading control device 44 is connected to the imaging console 5. The reading control device 44 controls the switching portion of each pixel of the radiation detector 43 based on the image reading conditions inputted from the imaging console 5 and switches reading of the electric signal stored in each pixel to read the electric signals stored in the radiation detector 43, thus acquiring image data (a static image or image frame). The reading control device 44 outputs the acquired image data to the imaging console 5. The image reading conditions include, for example, the frame rate, frame interval, pixel size (binning size), image size (matrix size), and the like. The frame rate is the number of image frames acquired per second and is equal to the pulse rate. The frame interval is a period from the start of the operation of acquiring an image frame to the start of the operation of acquiring the next image frame once in successive imaging and is equal to the pulse interval.

Herein, the radiation irradiation control device 42 and reading control device 44 are connected to each other and exchange synchronization signals from each other for synchronizing the radiation irradiation operation and the image reading operation. Moreover, at dark reading, in which at least one dark image is acquired for calculating an offset correction coefficient used in later-described offset correction, the series of image reading operations including resetting, storing, data reading, and resetting are performed not in synchronization with the radiation irradiation operation in the absence of radiation. The above may be performed at a timing before the series of operation of dynamic imaging or after the series of operation of dynamic imaging.

Figure 11:
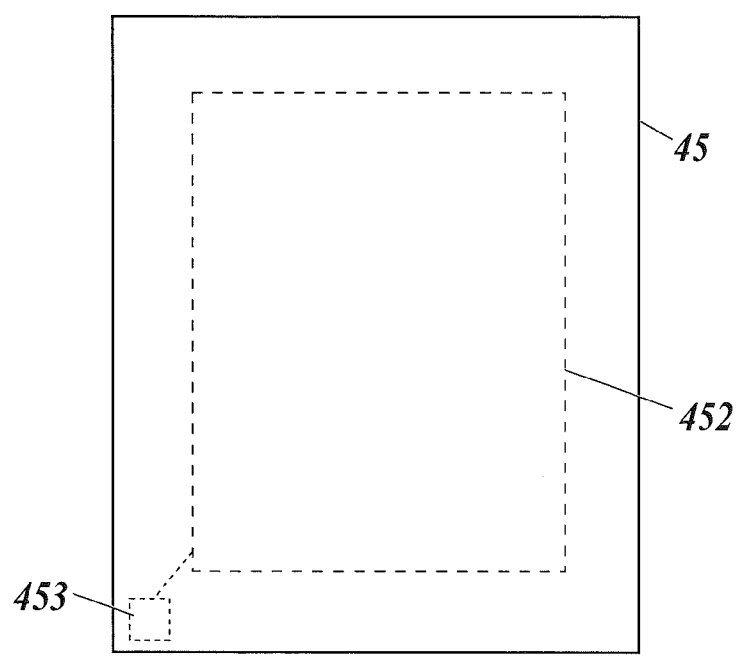
FIG. 11 is a schematic view illustrating the front of the holder 45 of FIG. 9.

As shown in FIG. 10, the holder 45 includes a detector holding portion 451 and holds the radiation detector 43 so that the radiation detector 43 faces the radiation source 41 and subject M at imaging. Moreover, the holder 45 further includes a grid attachment portion 452, for attaching a grid 46, which removes scattered radiation, to the subject's side of the radiation detector 43 (on the radiation source 41 side). The holder 45 is configured so that the grid 46 is detachable. The grid attachment portion 452 includes a grid attachment sensor MS (micro-switch) 453, which detects whether the grid 46 is attached, as shown in FIG. 11. The holder 45 outputs the detection signal of the grid attachment sensor MS 453 to the reading control device 44. The holder 45 further includes a subject detection sensor 454 which detects whether the subject M is situated at a predetermined distance as shown in FIG. 10. The holder 45 outputs a detection signal of the subject detection sensor 454 through the reading control device 44 to the imaging console 5.

[Configuration of Imaging Console 5]

The imaging console 5 outputs the radiation irradiation conditions and image reading conditions to the imaging apparatus 4 to control the radiation imaging and radiation image reading operation of the imaging apparatus 4 and properly creates images based on the static image or dynamic image acquired by the imaging apparatus 4, for example, preview images which are subjected to thinning and binning processing and processed images which are subjected to tone processing. The imaging console 5 then displays the same with which the imaging radiographer checks the positioning and determines whether the image is suitable for diagnosis.

As shown in FIG. 9, the imaging console 5 includes a control unit 51, a storage unit 52, an operation unit 53, a display unit 54, and a communication unit 55, which are connected through a bus 56.

The control unit 51 is composed of a CPU (Central Processing Unit), a RAM (Random Access Memory), and the like. In response to the operation at the operation unit 53, the CPU of the control unit 51 reads a system program and various processing programs stored in the storage unit 52 to be expanded in the RAM and executes the various processing, including a later-described imaging control processing, according to the expanded programs. The CPU thus performs centralized control of the operation of each section of the imaging console 5 and the radiation irradiation operation and reading operation of the imaging apparatus 4.

The storage unit 52 is composed of a non-volatile semiconductor memory, a hard disk, or the like. The storage unit 52 stores various programs executed by the control unit 51, parameters necessary for the programs to execute the processing, or data including processing results, etc. For example, the storage unit 52 stores an imaging control processing program to execute the imaging control process shown in FIG. 12A and FIG. 12B. The various programs are stored in the form of readable program code, and the control unit 51 sequentially executes operations according to the program code.

Moreover, the storage unit 52 stores the radiation irradiation conditions and image reading conditions for dynamic imaging and for static imaging.

The operation unit 53 is provided with a keyboard including cursor keys, numeric input keys, and various function keys and a pointing device such as a mouse. The operation unit 53 outputs to the control unit 51, instruction signals inputted by a key operation on the keyboard and a mouse operation. The operation unit 53 may include a touch panel on the display screen of the display unit 54. In this case, the operation unit 53 outputs to the control unit 51, instruction signals inputted through the touch panel.

The display unit 54 is composed of a monitor such as a LCD (Liquid Crystal Display) or a CRT (Cathode Ray Tube) and displays instructions inputted from the operation unit 53, data, and the like according to instructions of display signals inputted from the control unit 51.

The communication unit 55 includes a LAN adapter, a modem, a TA (terminal adapter), and the like and controls data exchange among the devices connected to the communication network NT2.

[Configuration of Diagnostic Console 6]

The diagnostic console 6 is a computer apparatus which acquires a static image or a series of image frames of a dynamic image from the imaging console 5 and displays the acquired image and diagnosis assistance information including a later-described histogram for interpretation and diagnosis by a physician.

As shown in FIG. 9, the diagnostic console 6 includes a control unit 61, a storage unit 62, an operation unit 63, a display unit 64, and a communication unit 65, which are connected through a bus 66.

The control unit 61 is composed of a CPU, a RAM, and the like. In response to operations at the operation unit 63, the CPU of the control unit 61 reads a system program and various processing programs stored in the storage unit 62 to be expanded in the RAM and executes various processing including a later-described image analysis processing according to the expanded programs. The CPU thus performs centralized control for the operation of each section of the diagnostic console 6.

The storage unit 62 is composed of a non-volatile semiconductor memory, a hard disk, or the like. The storage unit 62 stores various programs including an image analysis processing program used by the control unit 61 to execute the image analysis processing, parameters necessary for the programs to execute the processing, or data including processing results. These various programs are stored in the form of a readable program code, and the control unit 61 sequentially executes operations according to the program code.

The operation unit 63 is provided with a keyboard including cursor keys, numeric input keys, and various function keys and a pointing device such as a mouse. The operation unit 63 outputs to the control unit 61, instruction signals inputted by a key operation on the keyboard and a mouse operation. The operation unit 63 may include a touch panel in the display screen of the display unit 64. In this case, the operation unit 63 outputs to the control unit 61, instruction signals inputted through the touch panel.

The display unit 64 is composed of a monitor such as a LCD or a CRT and displays an instruction inputted from the operation unit 63, data, or the like according to instructions of display signals inputted from the control unit 61.

The communication unit 65 includes a LAN adapter, a modem, a TA, and the like and controls data exchange among the devices connected to the communication network NT2.

[Operation of Radiation Imaging System 200]

Next, a description is given of the operation of the radiation imaging system 200.

(Operations of Imaging Apparatus 4 and Imaging Console 5)

First, a description is given of imaging operation by the imaging apparatus 4 and imaging console 5.

Figure 12A:
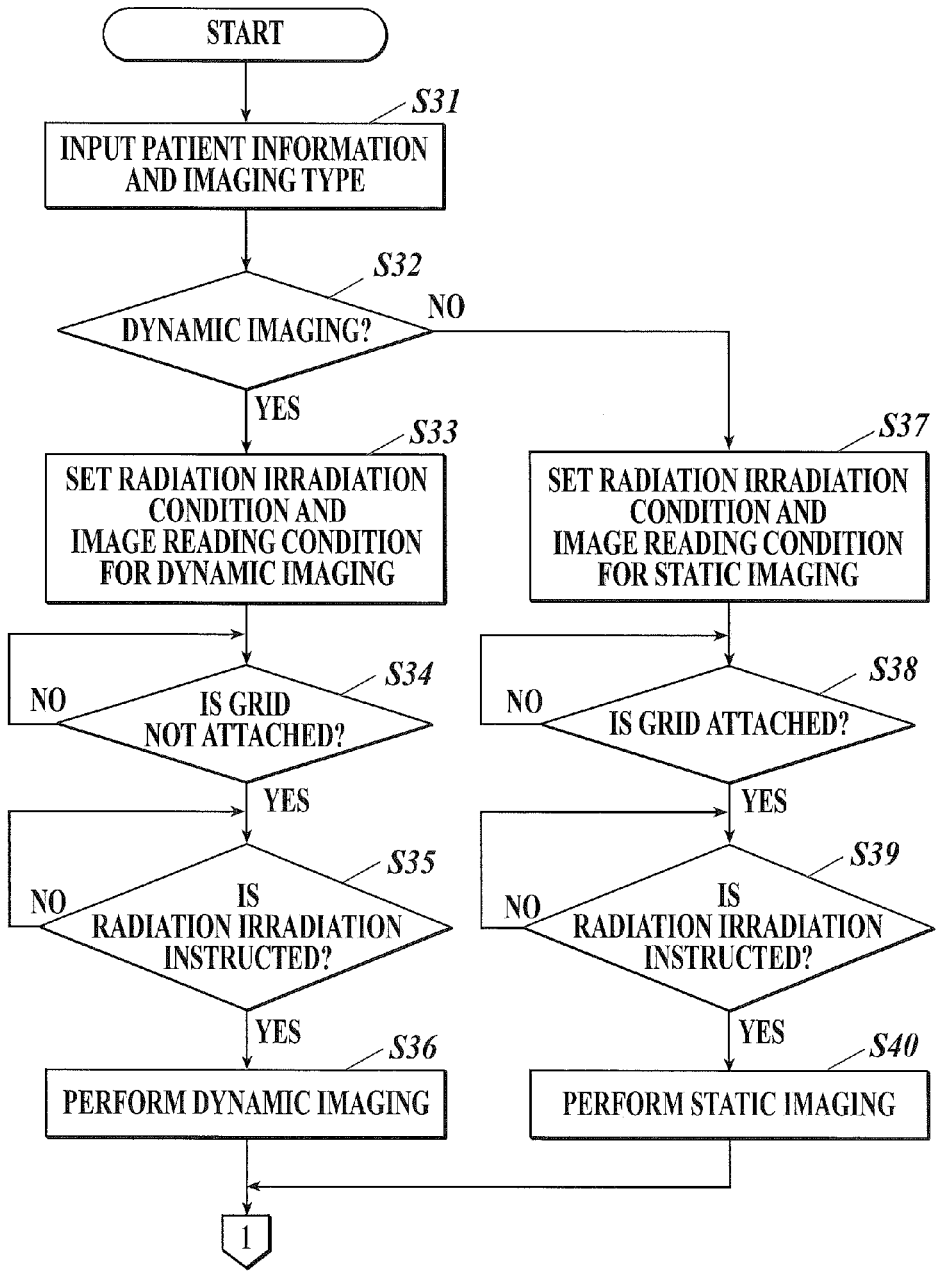
FIG. 12A is a flowchart illustrating an imaging control processing executed by a control unit of an imaging console of FIG. 9.
Figure 12B:
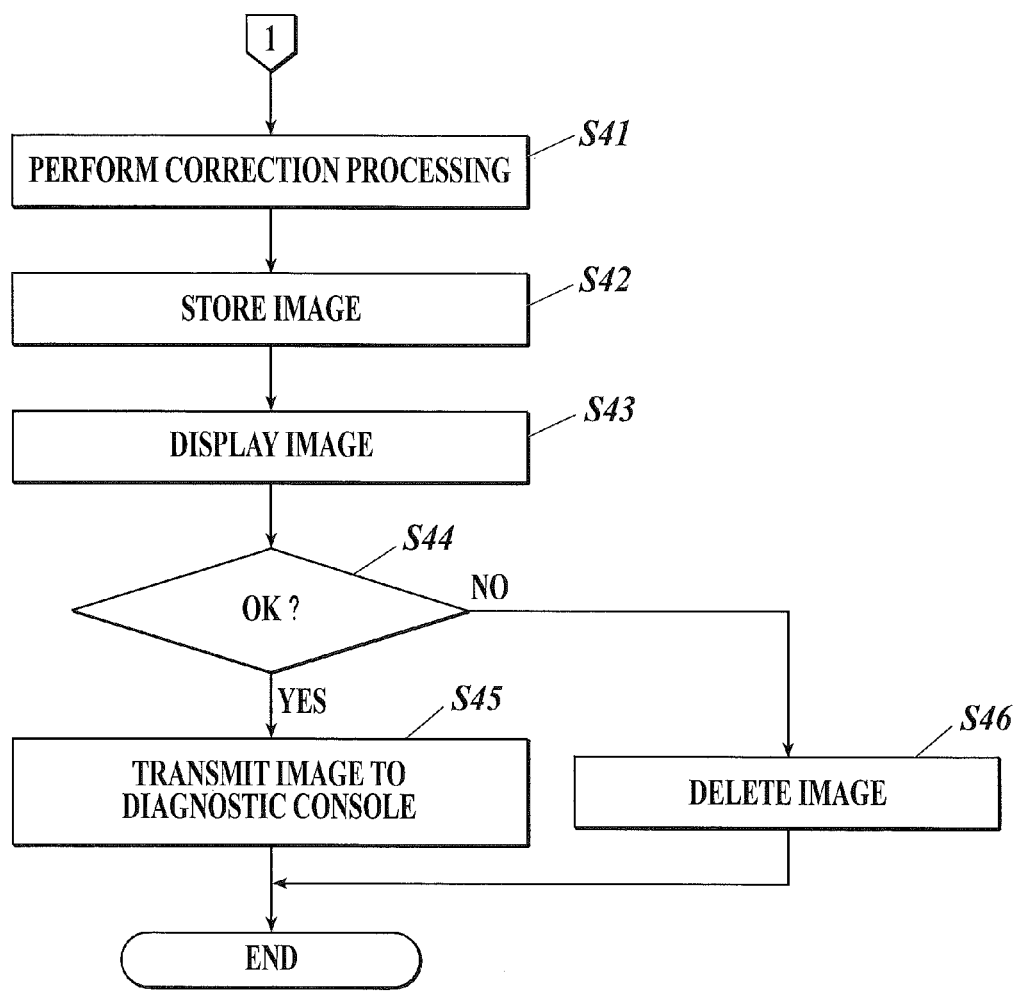
FIG. 12B is a flowchart illustrating the imaging control processing executed by the control unit of the imaging console of FIG. 9.

FIG. 12A and FIG. 12B show the imaging control processing executed by the control unit 51 of the imaging console 5. The imaging control processing is executed by the control unit 51 in cooperation with an imaging control processing program stored in the storage unit 52.

At first, a radiographer operates the operation unit 53 of the imaging console 5, and inputs patient information (patient's name, height, weight, age, sex, and the like) of an imaging target (the subject M) and imaging type (dynamic imaging or static imaging) (step S31). In addition, data transmitted from another not-shown device connected to the communication network NT2 and received through the communication unit 55 can be similarly inputted as input information.

Next, it is determined whether the inputted imaging type is dynamic imaging or static imaging (step S32). If it is determined that the inputted imaging type is dynamic imaging (step S32; YES), the radiation irradiation conditions for dynamic imaging is read from the storage unit 52 and are set in the radiation irradiation control device 42, and the image reading conditions for dynamic imaging are read from the storage unit 52 and are set in the reading control device 44 (step S33). If it is determined that the inputted imaging type is static imaging (step S32; NO), the radiation irradiation conditions for static imaging are read from the storage unit 52 and are set in the radiation irradiation control device 42, and the image reading conditions for static imaging are read from the storage unit 52 and are set in the reading control device 44 (step S37).

In this embodiment, the radiation irradiation conditions for dynamic imaging are set on the premise of imaging with the grid 46 not attached (without a grid), and the radiation irradiation conditions for static imaging are set on the premise of imaging with the grid 46 attached (with a grid). Specifically, the radiation irradiation conditions for dynamic imaging are set so that the dose reaching the radiation detector 43 in the absence of the grid 46 at imaging of each image frame is equal to the dose reaching the radiation detector 43 in the presence of the grid 46 at static imaging. In dynamic imaging, the radiation irradiation conditions are set so that the irradiation dose per image frame is smaller than that in static imaging.

Herein, in the case of irradiating the subject M such as a human body with radiation for radiation imaging, radiation transmitted through the body is scattered by body tissues. If such scattered radiation enters the radiation detector 43, noise occurs in the radiation image. Accordingly, at imaging of a static image, which is used in detection and observation of lesions and the like and has an importance on absolute output values (signal values) of individual pixels, it is preferable that imaging is performed with the grid 46 provided on the surface of the radiation detector 43 on the subject's side, that is, the surface on which the radiation transmitted through the subject enters. If imaging is performed in the presence of the grid, the dose reaching the radiation detector 43 is attenuated by the grid 46 (for example, the dose is attenuated to about a half by a grid having an exposure factor of 2), and it is therefore necessary to irradiate radiation increased by a dose to be attenuated by the grid. Conventional dynamic imaging also uses a grid in a similar manner to static imaging.

However, in the case of dynamic imaging, the number of imaged image frames is larger than that of static imaging. Accordingly, if the irradiation dose irradiated from the radiation source 41 to each image frame is equal to that of static imaging, there is a problem that the subject M is exposed to higher dose. For the purpose of reducing the exposure dose of the subject M, there is a disclosure of a technique of setting the irradiation dose of one static imaging equal to that of the total dose of a series of dynamic imaging. In this case, the dose of each image frame tends to be insufficient, and the S/N ratio is reduced.

Accordingly, after careful studies, the inventors found that chest movement images acquired by dynamic imaging are mainly used in movement analyses for the ventilation function, blood flow, and the like, and in these analyses, the results from the dynamic image imaged without a grid are substantially equal to those from the dynamic image imaged with a grid. In other words, regardless of the presence of a grid, it is possible to obtain substantially equal analysis results if the same dose reaches the radiation detector (see FIG. 13, described later in detail).

Based on these findings, in the radiation imaging system 200 of this embodiment, static imaging is performed with the grid 46 attached (with a grid), and dynamic imaging is performed with the grid 46 not attached (without a grid). By performing imaging under such radiation irradiation conditions that the dose reaching the radiation detector 43 at static imaging using the grid 46 is substantially equal to that of one frame at dynamic imaging not using the grid 46, the exposure dose of the subject M is reduced while the dose reaching the radiation detector 43 is maintained substantially equal to that of the conventional one. Alternatively, static imaging is performed with a grid while dynamic imaging is performed without a grid under such radiation irradiation conditions that the irradiation dose at one static imaging is equal to the total irradiation dose of a series of dynamic imaging. This can increase the S/N ratio of each image frame compared with the conventional method and therefore increase the analysis accuracy.

If the radiation irradiation conditions and image reading conditions for dynamic imaging are set, based on the output from the grid attachment detection MS 453, it is determined whether it is a state where the grid 46 is not attached to the grid attachment portion 452 (step S34).

If it is determined that the grid 46 is not attached to the grid attachment portion 452 (step S34; YES), an instruction to irradiate radiation by the operation of the operation unit 53 is waited (step S35). Herein, the radiographer instructs the examinee (subject M) to be relaxed and urges quiet breathing for imaging movements during quiet breathing. At the time when the preparation for imaging is completed, the radiographer operates the operation unit 53 to input an instruction to irradiate radiation.

When the instruction to irradiate radiation is inputted from the operation unit 53 (step S35; YES), an instruction to start imaging is outputted to the radiation irradiation control device 42 and reading control device 44 to start dynamic imaging (step S36). Specifically, radiation is irradiated from the radiation source 41 at the pulse intervals set in the radiation irradiation control device 42, and the radiation detector 43 acquires image frames. When imaging of the previously determined number of frames is finished, the control unit 51 outputs an instruction to terminate imaging to the radiation irradiation control device 42 and reading control device 44, thus stopping the imaging operation. The number of imaged image frames is at least the number of image frames which can be imaged in one breathing cycle.

On the other hand, if the radiation irradiation conditions and image reading conditions for static imaging are set, based on the output from the grid attachment detection MS 453 and subject detection sensor 454, it is determined whether the grid 46 is attached to the grid attachment portion 452 (step S38).

In this step S38, the control unit 51 makes control of preventing static imaging from being carried out in the absence of the grid 46.

If it is determined that the grid 46 is attached to the grid attachment portion 452 (step S38; YES), an instruction to irradiate radiation by the operation of the operation unit 53 is waited (step S39). Herein, the radiographer instructs the examinee to breathe in and then hold the breath. At the time when the preparation for imaging is completed, the radiographer operates the operation unit 53 to input an instruction to irradiate radiation.

When the instruction to irradiate radiation is inputted by the operation unit 53 (step S39; YES), an instruction to start imaging is outputted to the radiation irradiation control device 42 and reading control device 44 to perform static imaging (step S40).

When the dynamic imaging or static imaging is finished, each image (each image frame or static image) acquired by the imaging is sequentially inputted into the imaging console 5 for a correction processing (step S41). In the correction processing of step S41, three correction processing including an offset correction processing, a gain correction processing, and a defective pixel correction processing are performed when needed. First, the offset correction processing is performed for each of the acquired images to remove the offset value due to dark current superposed on the acquired image. In the offset correction processing, for example, a previously stored offset correction coefficient is subtracted from each pixel value (a density value, referred to as a signal value hereinafter) of each acquired image. Herein, the offset correction coefficient is an image obtained by averaging a plurality of image frames previously acquired in the absence of radiation. Subsequently, the gain correction processing is performed to remove variations in pixels due to individual differences of the detection elements corresponding to the pixels of each acquired image or variations in the gains of readout amplifiers. In the gain correction processing, for example, each image after the offset correction is multiplied by a previously stored gain correction coefficient. Herein, the gain correction coefficient is a coefficient previously calculated and stored based on the relationship between an image that is an average of the plurality of offset-corrected images acquired when uniform radiation is irradiated on the radiation detector 43 and output signal values which are expected under the radiation irradiation conditions in this process so that each pixel after the gain correction has a same signal value. Subsequently, the defective pixel correction processing is performed to remove pixels having non-linear sensitivity compared with pixels therearound and missing pixels having no sensitivity. In the defective pixel correction processing, for example, according to a previously stored defective pixel positional information map, the signal value of each defective pixel registered in the defective pixel positional information map is replaced with an average value of signal values of adjacent non-defective pixels. Herein, the defective pixel positional information map is a map registering the positions of a plurality of defective pixels previously recognized from the image frames which are obtained by irradiating the radiation detector 43 with uniform radiation and are then subjected to the offset correction and gain correction. The offset correction coefficient and gain correction coefficient and defective pixel positional information map have optimal values previously stored depending on acquisition modes including the binning, and dynamic range. The optimal values corresponding to each acquisition mode are read out. The aforementioned correction processing can be omitted to shorten the processing time. Moreover, preferably, the acquired images are subjected to thinning processing, gradation processing, or the like as needed.

Subsequently, the images after the correction processing are stored in the storage unit 52 (step S42) and are displayed in the display unit 54 (step S43). In the case of dynamic imaging, the image frames and the numbers indicating the order of imaging are correlated with each other and stored in the storage unit 52. Herein, the acquired images may be subjected to a logarithmic conversion process, which converts the signal value of each pixel from an antilogarithm to a logarithm just before the acquired images are stored. The radiographer checks the positioning and the like based on the displayed dynamic image and determines whether the image obtained by imaging is suitable for diagnosis (imaging: OK) or retaking is necessary (imaging: NG). The radiographer operates the operation unit 53 to input the determination result. The image frames acquired by the imaging may be collectively inputted after imaging of all the images is finished.

If the determination result indicating that imaging is OK is inputted by a predetermined operation of the operation unit 53 (step S44: YES), additional information such as the identification ID for identifying the image, the patient information, the examination target portion, the radiation irradiation conditions, the image reading conditions, the number showing the order of imaging, the imaging date, and information indicating the presence/absence of a grid at imaging (grid presence information) is attached to each of the static image acquired by static imaging or the series of image frames obtained by dynamic imaging (for example, the information is written in the header area of image data in a DICOM format). The images are then transmitted to the diagnostic console 6 through the communication unit 55 (step S45). The processing is thus terminated. On the other hand, when the determination result indicating that imaging is NG is inputted by a predetermined operation of the operation unit 53 (step S44; NO), the series of image frames stored in the storage unit 52 are deleted (step S46), and the processing is terminated. In this case, retaking is executed.

[Operation of Diagnostic Console 6]

Next, a description is given of the operation of the diagnostic console 6.

In the diagnostic console 6, if the static image is received from the imaging console 5 through the communication unit 65 and an instruction to display the received image is inputted through the operation unit 63, the received static image is displayed on the display unit 64 and is provided for physicians' diagnosis.

On the other hand, if the diagnostic console 6 receives the series of image frames of a dynamic image from the imaging console 5 through the communication unit 65 and is instructed through the operation unit 63 to perform movement analysis, the control unit 61 executes the image analysis processing in cooperation with an image analysis processing program stored in the storage unit 62.

In the image analysis processing of the second embodiment, processing steps are roughly the same as those of the image analysis processing shown in FIG. 3 in the first embodiment but are different in detail. Hereinafter, the image analysis processing is described with reference to FIG. 3 and FIG. 13 and drawings following FIG. 13.

First, lung field regions are extracted from each image frame (step S51). Next, the lung field regions of each image frame are divided into plurality of sub-regions, and the sub-regions of each image frame are correlated with sub-regions of the other image frames (step S52). The concrete processing in steps S51 to S52 are the same as that described in steps S21 and S22 of FIG. 3 in the first embodiment, and the description thereof is incorporated.

Next, the analysis is performed for the sub-regions correlated in step S52 in the series of image frames to calculate the inspiratory feature quantity and the expiratory feature quantity (step S53). Herein, as the inspiratory feature quantity and the expiratory feature quantity, for example, representative values (maximum values of the absolute values) of inter-frame difference values (differential values) of each sub-region during the inspiratory period and the expiratory period are calculated. The inter-frame difference values are values representing signal changing amounts at the timing when the image frame of interest is imaged. When air is inhaled and exhaled in breathing, the density in the lungs changes with the flow of breath, and the amount of transmitted X-ray (that is, signal values outputted from pixels) changes. The signal changing amounts can be considered as values representing the airflow rate at the timing. The representative values are not limited to the maximum absolute value but also may be a center value, an average value, or a mode value.

Specifically, first, the signal values (average signal values) of pixels of each sub-region in each image frame are calculated.

Subsequently, the sub-regions correlated in the image frames are subjected to a chronological filtering processing. This filtering processing is a processing to remove high frequency changes in signal due to bloodstream or the like and extract changes in signal values with time due to ventilation. For example, for changes in signal values in each sub-region with time, low-pass filtering is performed by using a cutoff frequency of 0.7 Hz in the group of images at quiet breathing and a cutoff frequency of 0.5 Hz in the group of images at deep breathing. Herein, it is preferable that the cutoff frequency of the low-pass filter is optimized for each imaged dynamic image instead of being fixed. For example, the cutoff frequency of the low-pass filter is calculated as follows. As described above, the positions of the diaphragm in the series of image frames are analyzed, and in the case of quiet ventilation, frames at the resting expiratory level and inspiratory level are detected. Based on the number of frames between the frame at the resting expiratory level and the frame at the next resting expiratory level, the duration time of the inspiratory period is calculated, and the reciprocal of the calculated time is multiplied by a predetermined coefficient as the cutoff frequency. In the case of resting ventilation, it is preferable that the cutoff frequency automatically set is limited to a range of 0.2 to 1.0 Hz. Alternatively, in step S31, vital signs separately measured at rest, such as the number of breathes per minute and pulse rates may be input as patient information and the cutoff frequency may be calculated based on the above values. For example, the low pass filter may be implemented with a cut-off frequency obtained as follows. The number of breaths per minute inputted as the patient information is converted into the number of breaths per second, and the number of breaths per second is multiplied by a predetermined coefficient as the cut-off frequency. Furthermore, the low pass filter may be implemented with a cut-off frequency obtained as follows. The inputted number of pulses per minute is converted into the number of pulses per second, and the number of breaths per second and the number of pulses per second are averaged as the cut-off frequency.

After the filtering processing, the inter-frame difference process is performed to calculate the difference between signal values of the corresponding sub-regions in the image frames next to each other in the order of imaging. In this process, a difference value (N+1−N) of the image frames of frame numbers N and N+1 (N is 1, 2, 3, . . . ) is calculated for each sub-region of the image frame N. The maximum value (the maximum value of the absolute value) of the inter-frame difference values in the expiratory period is acquired as the expiratory feature quantity, and the maximum value (the maximum value of the absolute value) of the inter-frame difference values in the inspiratory period is acquired as the inspiratory feature quantity. The maximum value (the maximum value of the absolute value) of the inter-frame difference values is equivalent to the maximum differential value. Herein, the period where the inter-frame difference value in each sub-region is positive is to be the inspiratory period and the period where the inter-frame difference value in each sub-region is negative is to be the expiratory period.

Next, the value of the ratio of the inspiratory feature quantity to the expiratory feature quantity (inspiratory feature quantity/expiratory feature quantity) is calculated for each sub-region (step S54). In this process, "maximum value of the inter-frame difference values in the inspiratory period/maximum value of the inter-frame difference values in the expiratory period" (called a maximum flow rate ratio) is calculated.

Next, a histogram of the calculated values of the "inspiratory feature quantity/expiratory feature quantity" of each sub-region is created. Moreover, the index values (average values, standard deviations) representing the tendency of the "inspiratory feature quantity/expiratory feature quantity" in the entire lung field are calculated (step S55). In the histogram, it is preferable that the number of counts in the axis of ordinate is divided by the number of all the sub-regions in the lung fields for normalization.

Next, the values of the "inspiratory feature quantity/expiratory feature quantity" calculated for each sub-region are converted to display parameter values based on a conversion table of values of the "inspiratory feature quantity/expiratory feature quantity" and parameter values at display, which is stored in the storage unit 62 in advance. Based on the converted parameter values, an image displaying each sub-region of the referential image (the image frame at the resting expiratory level, for example) is created (step S56). The conversion table is, for example, a table correlating threshold values which are used to specify the range of feature quantity magnitude of each category when classifying the feature quantities to normal/abnormal categories (severities 1 to n) (threshold values for categories) with any of hues, intensities, luminances, and transparencies one to one. Herein, the conversion table of the display parameter values preferably correlates the threshold value of each category with a hue in order to enhance ability of discrimination of the magnitude of the feature quantities.

At this time, for example, some of the threshold values of the categories are correlated with several hues (five or six hues, for example), and the value of the feature quantity between the thresholds are related to intermediate hues (the hues are gradated), thus implementing display providing high quality in ability of discrimination.

The image colored based on the display parameter values may be displayed overlaid on the image frame set as the referential image.

The storage unit 62 stores a conversion table corresponding to dynamic images imaged in the presence of a grid and a conversion table corresponding to dynamic images imaged in the absence of a grid. In steps S56 and S57, based on the grid presence information attached to the series of image frames, it is determined whether the dynamic image is imaged in the presence or absence of a grid. The image is colored using the conversion table depending on the determination result.

The created histogram, the created static image, and the like are displayed side by side on the display unit 64 (step S57), and the image analysis processing is terminated. The region of the histogram is displayed colored based on the same criteria as the sub-regions of the lung field regions of the referential image according to the aforementioned conversion table of values of the "inspiratory feature quantity/expiratory feature quantity" and display parameter values.

Herein, a description is given of the influence of imaging with a grid and imaging without a grid on the analysis of movements.

Figure 13:
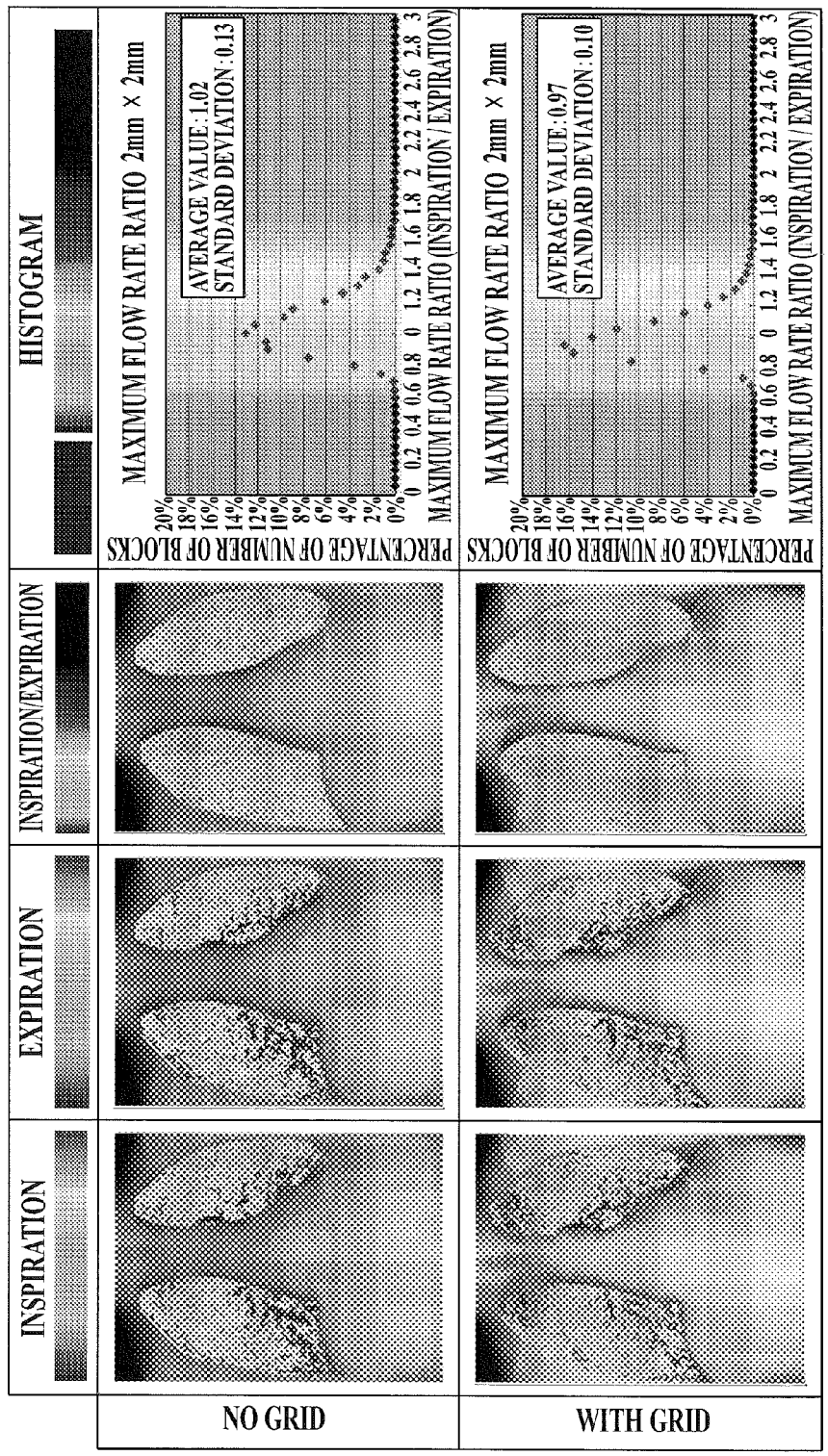
FIG. 13 is a view illustrating a comparison between results from movement analyses for dynamic images of normal lung fields which are imaged with a grid and without a grid.

FIG. 13 is a diagram illustrating the comparison between movement analysis results of dynamic images of normal lungs imaged with a grid and imaged without a grid. As the analysis results, FIG. 13 shows: images of dynamic images imaged with a grid and imaged without a grid in which sub-regions are colored based on the "maximum value of the inter-frame difference value in the inspiratory period" (maximum inspiratory flow rate); images of dynamic images imaged with a grid and imaged without a grid in which sub-regions are colored based on the "maximum value of inter-frame difference value in the expiratory period" (maximum expiratory flow rate); images of dynamic images imaged with a grid and imaged without a grid in which sub-regions are colored based on the maximum flow rate ratio; and the histogram of the maximum flow rate ratio.

FIG. 13 shows the analysis results of dynamic images imaged under the following imaging conditions: the detector size, 40×30 cm; the detector pixel size, 194 μm; the grid pitch, 80 line/cm; the grid ratio, 12/1; the bulb-to-detector distance, 2 m; the number of frames, 75 (imaged in about 10 seconds); and the total exposure dose (the subject exposure dose when the dose reaching the detector is constant) with a grid, 0.24 mGy; and the total exposure dose without a grid, 0.14 mGy.

As for the tables converting the magnitudes of the maximum inspiratory flow rate, maximum expiratory flow rate, and maximum flow rate ratio to colors (represented by density in FIG. 13), the same table (herein, the conversion tables for imaging with a grid) is used to compare the both.

The dynamic images of a same subject imaged with a grid and without a grid are substantially the same in terms of the maximum inspiratory flow rate, the maximum expiratory flow rate, and the maximum flow rate ratio but have a little difference depending on the characteristics of the imaging system and the like in some cases as shown in FIG. 13. For example, in FIG. 13, the shape of the histogram of the dynamic image imaged without a grid is wider than the shape of the histogram of the dynamic image imaged with a grid. Accordingly, if the region of the lung fields or the region of the histogram is classified into normal to abnormal categories 1 to n and colored in terms of the maximum flow rate ratio, for example, by using the same threshold values (conversion tables) for the images imaged with a grid and imaged without a grid, the sub-regions having a same maximum flow rate ratio could be displayed in different colors, that is, could be classified into different severities in some cases, which is not preferred. As shown in FIG. 13, in the case where dynamic images imaged with a grid and imaged without a grid have a difference that influences diagnosis, it is necessary to change the threshold values (the conversion table) used to classify the feature quantities depending on the presence or absence of a grid.

The amount of difference between the results from the analysis for the dynamic images imaged with a grid and the results from the analysis for the dynamic images imaged without a grid differs depending on the characteristics of the imaging system, the analysis contents, and the like. It is therefore preferable to analyze a plurality of images of a same subject imaged with a grid and imaged without a grid by the imaging system and using the analysis results to recursively calculate threshold values used for dynamic images imaged with a grid and threshold values used for dynamic images imaged without a grid.

In the present embodiment, the imaging apparatus 4 is controlled so as to image dynamic images without a grid. Accordingly, it is considered to be enough if the threshold values for dynamic images imaged without a grid are stored. However, the diagnostic console 6 can be connected to an imaging system capable of imaging dynamic images with a grid. In this case, when the presence or absence of a grid in the imaging conditions is different, a false judgment may be made. In the present embodiment, therefore, the grid presence/absence information is attached as the additional information of each image frame constituting dynamic images in advance. The control unit 61 performs analyses based on the grid presence/absence information, with an analysis algorithm using threshold values depending on the presence/absence of a grid at imaging.

Moreover, there could be a case of comparing the analysis results of a past image and the current analysis results of a same patient. When the grid presence/absence information is attached to both images, it is preferable that the values of one of the analysis results are corrected and used (for example, the differences between the threshold values of both conversion tables are added to or subtracted from the feature quantities as the analysis result) so that one of the analysis results is comparable with the other analysis result.

Figure 14A:
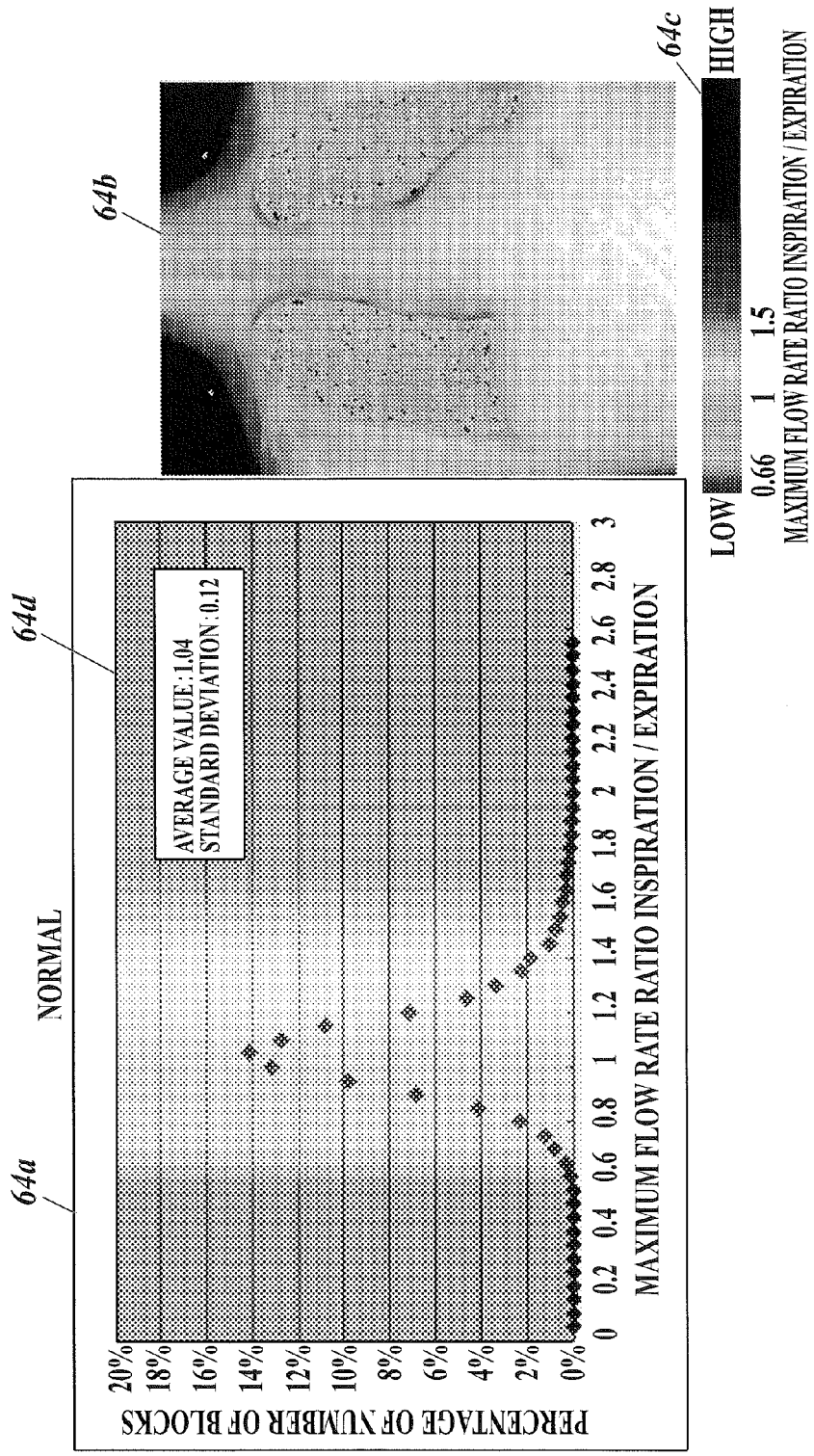
FIG. 14A is a view illustrating an example of a display screen that displays analysis results from the analysis for a dynamic image of lung fields of a normal subject in the second embodiment.
Figure 14B:
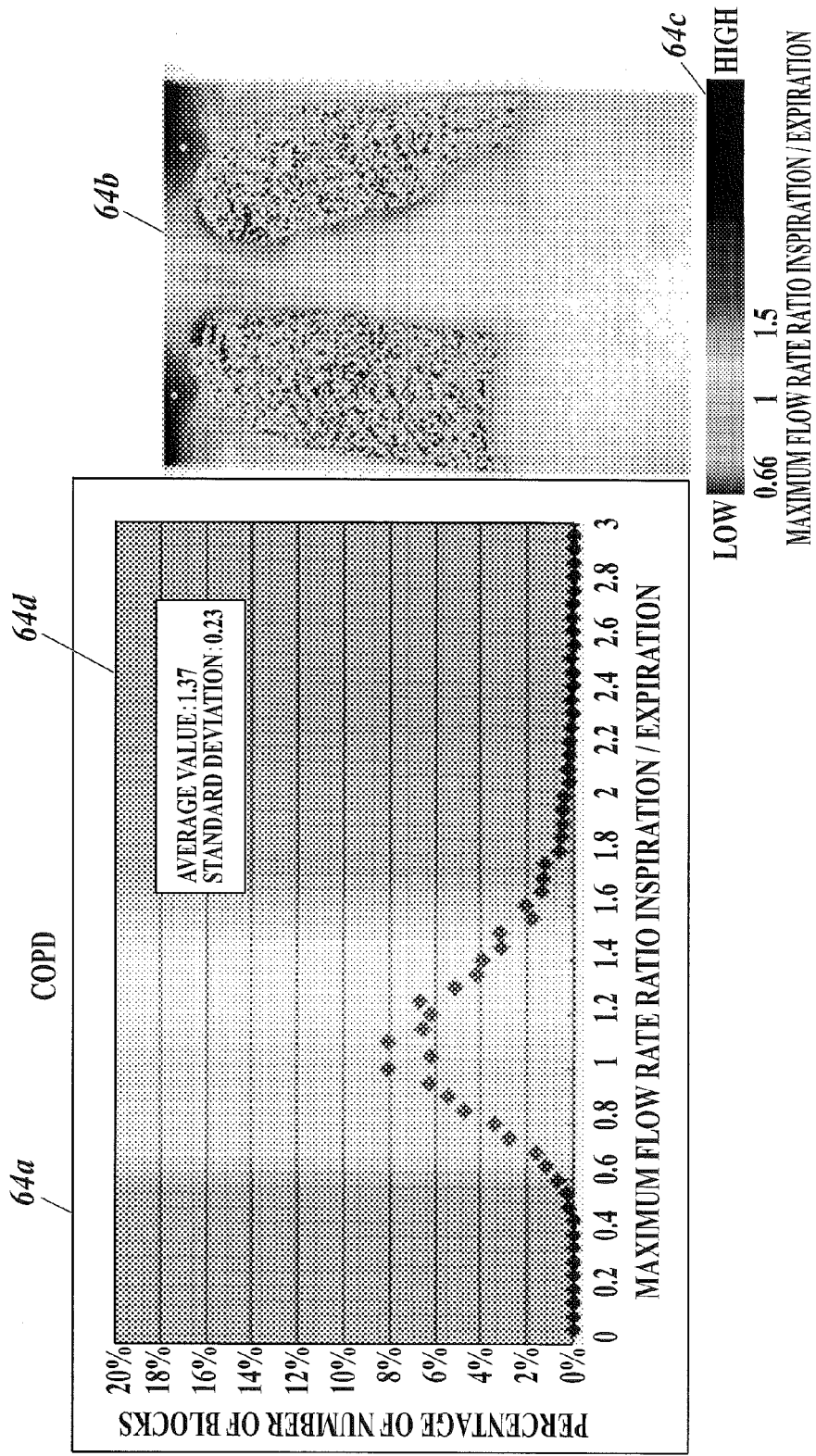
FIG. 14B is a view illustrating an example of a display screen that displays analysis results from the analysis for a dynamic image of lung fields in COPD (chronic obstructive pulmonary disease) in the second embodiment.
Figure 14C:
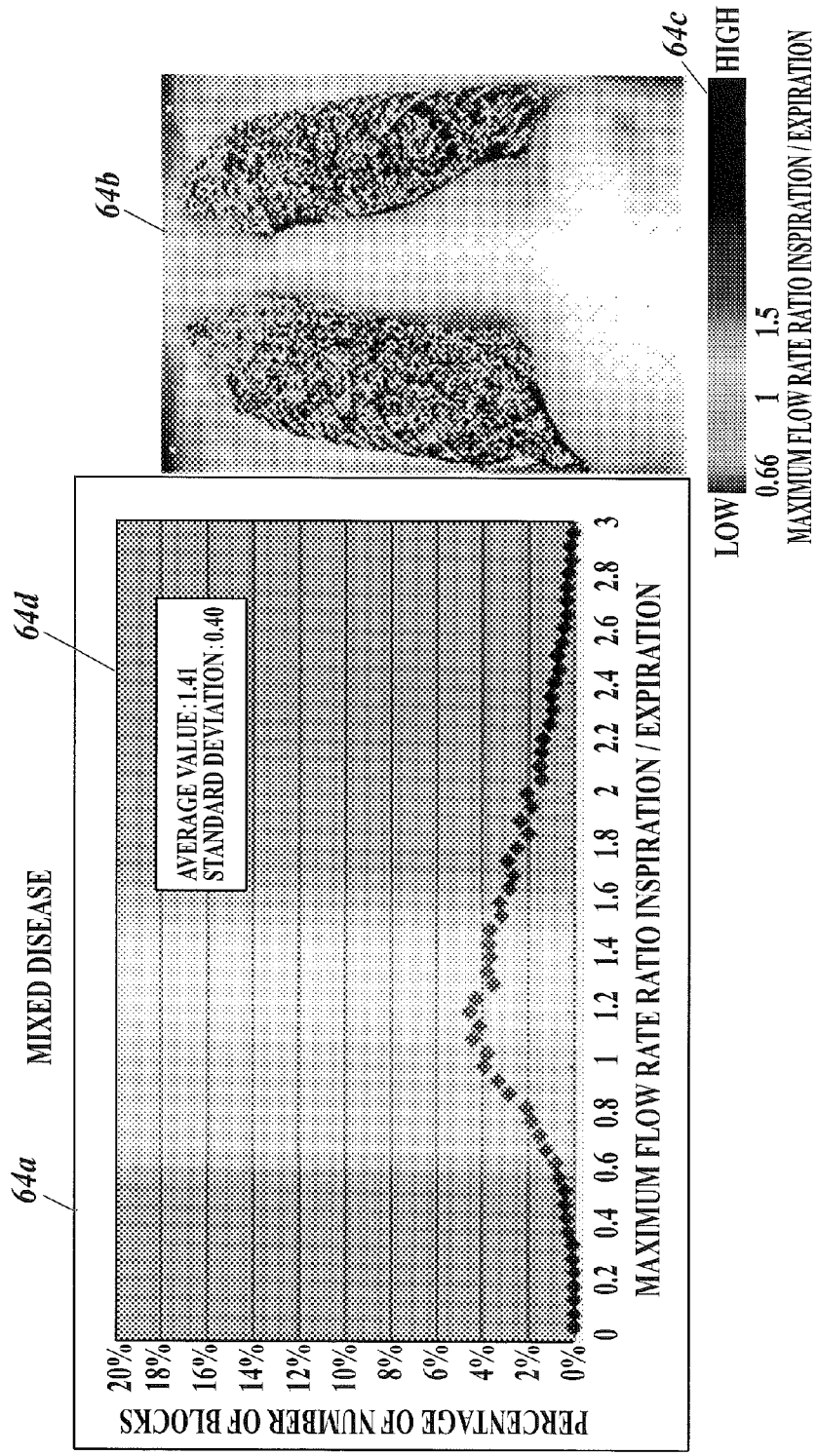
FIG. 14C is a view illustrating an example of a display screen that displays analysis results from the analysis for a dynamic image of lung fields in mixed disease in the second embodiment.

FIG. 14A to FIG. 14C illustrate examples of display screens displayed in the display unit 64 in step S57.

FIG. 14A is a display screen displaying the analysis result from the analysis for a dynamic image of the lung fields of a normal subject imaged with a grid. FIG. 14B shows a display screen displaying the analysis result from the analysis for a dynamic image of the lung fields of COPD (obstructive disease). FIG. 14C is a display screen displaying the analysis result from the analysis for a dynamic image of the lung fields of mixed disease.

As shown in FIG. 14A to FIG. 14C, in step S57, a histogram 64a, a static image 64b, a display 64c, and an index value 64d are displayed. The histogram 64a is a histogram of values of the "inspiratory feature quantity/expiratory feature quantity" of sub-regions (2 mm rectangular size) in the lung field regions extracted from an image frame of half size. The static image 64b displays as a list the "inspiratory feature quantity/expiratory feature quantity" of each sub-region. The display 64c shows the relationship between the hues displayed in the histogram 64a and static image 64b and the values of the "inspiratory feature quantity/expiratory feature quantity". The index note 64c represents the tendency of the "inspiratory feature quantity/expiratory feature quantity" in the entire lung fields. As shown in FIG. 14A to FIG. 14C, in the histogram 64a, the region is displayed divided in the axis of abscissa direction and colored by six hues depending on the magnitude of the value of the "inspiratory feature quantity/expiratory feature quantity". Accordingly, physicians can easily understand the distribution of the "inspiratory feature quantity/expiratory feature quantity" in the lung fields at a glance of the histogram. In the static image 64b showing the "inspiratory feature quantity/expiratory feature quantity" of each sub-region, the sub-regions are displayed in colors defined based on the same criteria as those of the histogram depending on the values of the "inspiratory feature quantity/expiratory feature quantity". Accordingly, physicians can easily understand a locally abnormal portion (obstructive portion or restrictive portion) in the lung fields. Furthermore, as the index value 64a representing the tendency of the "inspiratory feature quantity/expiratory feature quantity" in the entire lung fields, the average value and standard deviation thereof are calculated and displayed together on the screen. This can provide physicians with a numerical value the tendency of the "inspiratory feature quantity/expiratory feature quantity" in the entire lung fields.

In the present display example, the axis of ordinate indicates the percentage of the number of occurrences of 2 mm-square small blocks to the number of all blocks ((430 mm/2 mm)×(354 mm/2 mm)=38055 blocks). However, as shown in FIG. 8, the axis of ordinate may indicate the number of occurrences of 2 mm-square small blocks. In the case where the detectors used in dynamic imaging have various sizes, the display of percentage, in which values are normalized by the total number of regions like this display example, is preferred because the analysis results for a same case can be displayed in a uniform fashion and is less likely to cause physicians and the like to make false recognition of the analysis results.

Herein, when the maximum value (absolute value) of the inter-frame difference values in the expiratory period is to be the expiratory feature quantity and the maximum value (absolute value) of the inter-frame difference values in the inspiratory period is to be the inspiratory feature quantity, as for the lung fields of a normal subject, it is known that the average value of the "inspiratory feature quantity/expiratory feature quantity" of the entire lung fields is 0.9 to 1.2 and the standard deviation thereof is about 0.10 to 0.22 in the analysis for a dynamic image imaged with a grid. Accordingly, if the display screen shown in FIG. 14A is displayed in step S57, physicians can easily understand that the imaged lung fields are normal.

On the other hand, as for the lung fields in COPD (obstructive disease), it is known that in the analysis for a dynamic image imaged with a grid, the average value of the "inspiratory feature quantity/expiratory feature quantity" is out of the range of 0.9 to 1.2 (larger than that of the normal subject) and the standard deviation thereof is out of the range of 0.10 to 0.22 (larger than that of the normal subject). Accordingly, if the display screen shown in FIG. 14B is displayed in step S57, physicians can easily understand that the imaged lung fields have COPD.

Furthermore, as for the lung fields having mixed lung disease, it is known that in the analysis for a dynamic image imaged with a grid, the number of pieces of data having values of "inspiratory feature quantity/expiratory feature quantity" of the entire lung fields which are not more than 0.66 and not less than 1.5 are increased. Accordingly, if the display screen shown in FIG. 14C is displayed in step S57, physicians can easily understand that the imaged lung fields have mixed disease.

In such a manner, the radiation imaging system 200 is capable of providing physicians with useful diagnostic information which can specify the clinical condition such as uneven ventilation of COPD (obstructive lung disease), mixed lung disease, and the like or the severity thereof from the index value representing the tendency of the "inspiratory feature quantity/expiratory feature quantity".

The normal/abnormal of the subject M may be judged using the index values representing the tendency of the "inspiratory feature quantity/expiratory feature quantity" and the like. Also in this case, it is preferable to change the threshold values for judging normal/abnormal states depending on the grid presence/absence information. When the normal/abnormal states are judged based on the average value of the "inspiratory feature quantity/expiratory feature quantity" of the entire lung fields, it is preferable to judge an average value of 0.9 to 1.2 to be normal in the presence of a grid, and an average value of 0.8 to 1.3 to be normal in the absence of a grid.

The expiratory feature quantity and the inspiratory feature quantity may be other than the aforementioned examples.

For example, the expiratory feature quantity may be the number of image frames corresponding to the expiratory period in one breathing cycle (expiratory time), and the inspiratory feature quantity may be the number of image frames corresponding to the inspiratory period in one breathing cycle (inspiratory time). Herein, if the ventilation function of lungs is normal, the expiratory time should be substantially equal to the inspiratory time or the expiratory time should be a little longer than the inspiratory time. Accordingly, by checking the values of the "number of image frames corresponding to the expiratory period/number of image frames corresponding to the inspiratory period", physicians can understand whether the lungs are suspected to have lung disease. Especially, it is found that the region of the "number of image frames of the expiratory period/number of image frames of the inspiratory period">1.5 is an obstructive portion in which ventilation through expiration is difficult to cause a delay in exhaling the taken air. The relationship of the "maximum value of the inter-frame difference value in the inspiratory period/maximum value of the inter-frame difference value in the expiratory period" expiratory time (the number of image frames of the expiratory period)/inspiratory time (the number of image frames of the inspiratory period) is satisfied. Accordingly, physicians can distinguish normal condition, COPD (obstructive lung disease), and mixed lung disease according to the judgment criteria similar to the case where the expiratory feature quantity is the maximum value of the inter-frame difference value in the expiratory period and the inspiratory feature quantity is the maximum value of the inter-frame difference value in the inspiratory period.

Alternatively, in each of the image frames of one breathing cycle, signal values (average signal values) of pixels of each sub-region are calculated, and the minimum value and the maximum value of the signal values of each sub-region are calculated in one breathing cycle. The calculated minimum value may be used as the expiratory feature quantity of the region and the maximum value may be used as the inspiratory feature quantity of the region. It can be thought that the difference between the maximum value and the minimum value of the signal values is large in the normal portion and the difference between the two is very small in the abnormal portion. This is because movement of the pulmonary alveoli becomes stiff in the abnormal portion and the change in density of the pulmonary alveoli becomes small. Accordingly, physicians refer to the histogram of the "maximum value of the signal value/minimum value of the signal value" and check the average value and standard deviation to determine whether the lung fields are normal or diseased. For example, if the average value of the "maximum value of the signal value/minimum value of the signal value" of the entire lung fields is more than 1 and the standard deviation thereof is small, it can be determined that the lungs function normally. On the other hand, if the average value of the "maximum value of the signal value/minimum value of the signal value" of the entire lung field is close to 1 and the standard deviation thereof is large, it can be determined that the lungs have a functional disorder.

Furthermore, in addition to the average value and standard deviation, the index value representing the tendency of the "inspiratory feature quantity/expiratory feature quantity" may be the value of "inspiratory feature quantity/expiratory feature quantity" at the peak of the number of counts (the number of blocks (sub-regions)) in the histogram or the number of counts (the number of blocks) at the peak or the ratio of the number of counts when the value of the "inspiratory feature quantity/expiratory feature quantity" is not less than a predetermined value to the number of counts when the value of the "inspiratory feature quantity/expiratory feature quantity" is not more than a predetermined value. Alternatively, a plurality of indexes may be combined to create a new index value.

As described above, according to the radiation imaging system 200, static imaging is performed using the grid 46, and dynamic imaging is performed without using the grid 46. This eliminates the attenuation of the dose due to a grid and, accordingly, the radiation detector 43 receives higher dose even when the same irradiation dose is sent to the subject. Accordingly, it is possible to perform high-definition moving image analyses. Moreover, when the dose reaching the radiation detector 43 is kept constant, the irradiation dose to the subject (the exposure dose of the subject) can be reduced compared with conventional dynamic imaging using a grid.

Moreover, each image frame obtained by dynamic imaging is accompanied with the grid presence/absence information, and the control unit 61 of the diagnostic console 6 changes the analysis algorithm, for example changes the threshold values used in the analysis, based on the grid presence/absence information. It is therefore possible to provide an accurate analysis result irrespective of the presence/absence of the grid at dynamic imaging.

The description in the above embodiment is merely a preferable example according to the present invention and does not limit the present invention.

For example, at imaging without a grid, in order to mitigate the influence of scattered radiation for better movement observation and movement analyses, it is therefore preferable that the subject M is located apart from the radiation detector 43 in the process of imaging. When imaging is performed with the subject M positioned apart from the radiation detector 43, the air gap can reduce the influence of scattered radiation. This provides magnified images because of the distance between the subject M and the radiation detector 43, but does not affect the movement analysis results. As described in Japanese Patent Publication No. 3861572, imaging may be performed under the imaging conditions of phase contrast imaging. At this time, dynamic imaging may be forbidden if the subject is in contact with the radiation detector 43 in the absence of a grid. Herein, whether the subject is separated from or in contact with the radiation detector 43 is detected with the subject detection sensor 454.

Moreover, in the above embodiments, as the analysis results of the "inspiratory feature quantity/expiratory feature quantity", the maximum flow rate ratio is displayed in a histogram, but the present invention is not limited to this.

Figure 15:
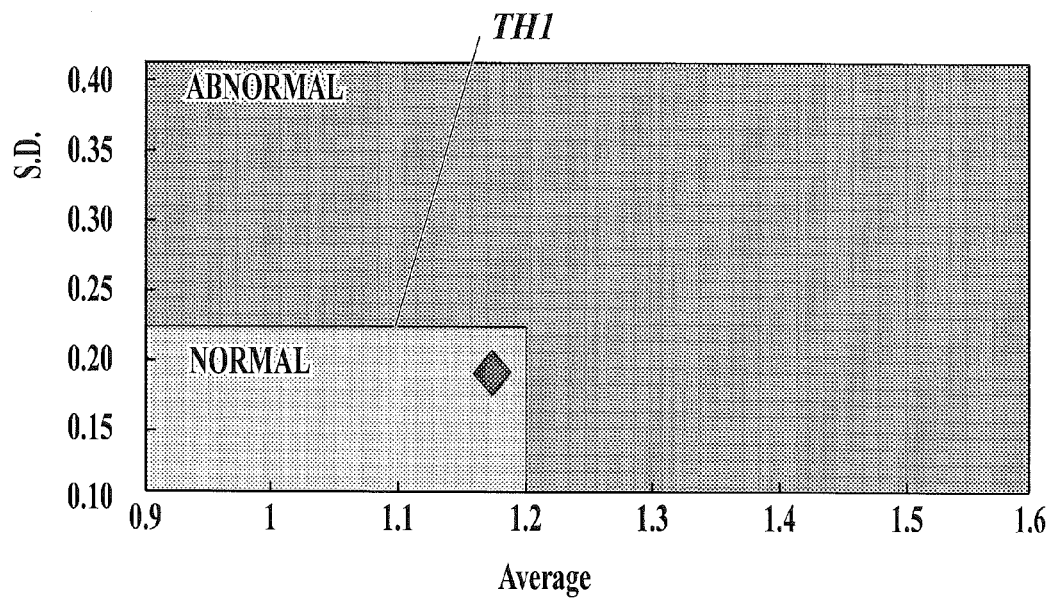
FIG. 15 is a diagram illustrating a display example of index values representing the tendency of "inspiratory feature quantity/expiratory feature quantity"

For example, as shown in FIG. 15, in a graph with the one of the index values representing the tendency of the "inspiratory feature quantity/expiratory feature quantity" on the axis X and the other index on the axis Y, threshold values TH1 between normal and abnormal states of the index values are shown. The analysis results may be displayed as a diagram in which index values representing the tendency of the "inspiratory feature quantity/expiratory feature quantity" of the entire lung field calculated from a dynamic image are plotted on the graph. FIG. 15 is a graph with the average value of "the maximum value of the inter-frame difference value in the inspiratory period/the maximum value of the inter-frame difference value in the expiratory period" on the axis X and the standard deviation thereof on the axis Y, plotting the index value of the average values and the standard deviations of the "inspiratory feature quantity/expiratory feature quantity" of the entire lung fields calculated from the dynamic image. By using such a graph to display the index values representing the tendency of the "inspiratory feature quantity/expiratory feature quantity", the abnormal degree can be visually understood easily by the distance between each plotted point and the threshold value TH1.

Figure 16:
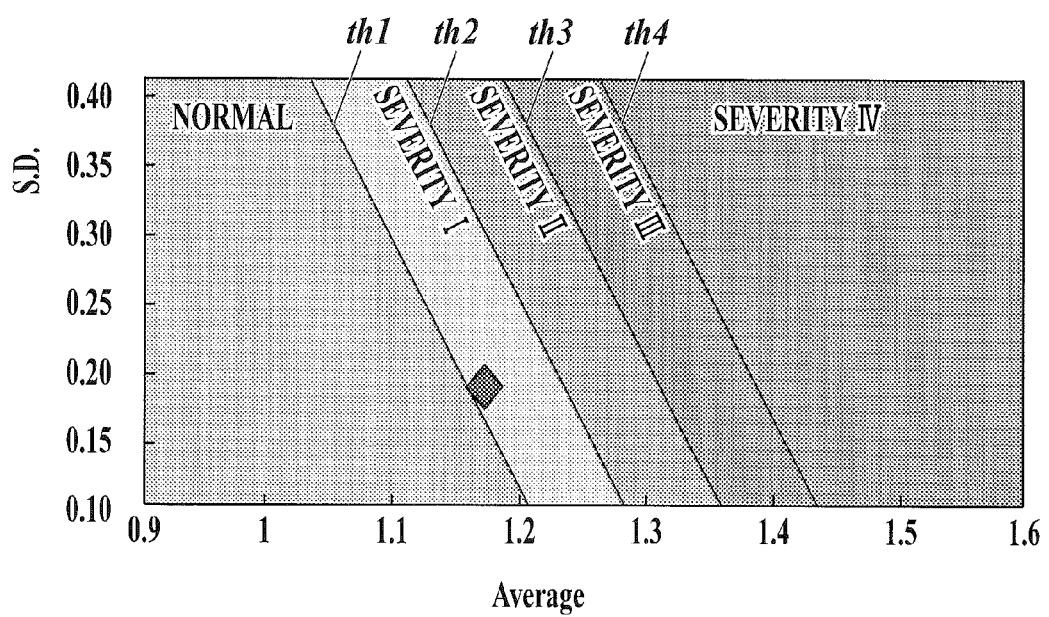
FIG. 16 is a diagram illustrating another display example of index values representing the tendency of "inspiratory feature quantity/expiratory feature quantity"

Alternatively, for example, two index values (for example, the average value and standard deviation of the "inspiratory feature quantity/expiratory feature quantity") may be linearly combined into a new index value. As shown in FIG. 16, in a graph with one of the two index values on the axis X and the other index value on the axis Y, threshold values th1 to th4 for classifying the new index value (the index value obtained by linearly combining two index values) based on the severity are indicated. The new index value calculated from a dynamic image may be plotted on the graph. As an example of the linear combination, the index value may be the first primary component calculated by a principal component analysis from data of a large number of pieces of measurement value data for the average value and standard deviation. By using such a graph, the abnormal degree can be visually understood more easily. Alternatively, the index value may be a primary component which is obtained by calculating the maximum specific value of a covariance matrix of NxM pieces of data from a large number of pieces of (N pieces) measurement value data for a plurality of (M index values) index values, for example.

Furthermore, in addition to the index value representing the tendency of the "inspiratory feature quantity/expiratory feature quantity", index values indicating the tendency of the inspiratory feature quantity or expiratory feature quantity may be calculated. For example, a static image as shown in FIG. 17 may be formed in the following manner. In terms of the inspiratory or expiratory feature quantity calculated for each sub-region, the coefficient of variation (=standard deviation/average value) is calculated for each of six regions dividing each of the right and left lung fields to three portions, upper, middle, and lower portions. These six regions are displayed colored in hues (or brightnesses, or luminances) according to the magnitudes of the calculated coefficients of variation. Such a display can facilitate understanding the distribution of uneven ventilation. It is therefore possible to easily judge whether the area of uneven ventilation is localized or diffused. Moreover, the above-described creation of a histogram, calculation of index values, and creation of an image colored based on the conversion table to display parameters may be performed for the value of "inspiratory feature quantity/expiratory feature quantity" converted to logarithm.

The above-described embodiment describes about the system including the imaging apparatus capable of performing both dynamic imaging and static imaging. However, even in an imaging apparatus capable of performing only dynamic imaging, imaging without a grid is effective on reduction in exposure dose of a subject and an improvement in image quality.

Moreover, for example, the above description discloses an example in which the computer-readable medium of the program according to the present invention is a hard disk, a semiconductor non-volatile memory, or the like. However, the present invention is not limited to this example. As another computer-readable medium, a portable recording medium such as CD-ROM can be applied. Moreover, as a medium providing data of the program according to the present invention through a communication line, carrier waves are applied.

Moreover, the detailed configuration and operation of each device constituting the thoracic diagnosis assistance system 100 and radiation imaging system 200 can be properly changed without departing from the spirit of the present invention.

The entire disclosure of Japanese Patent Application No. 2010-190241, filed on Aug. 27, 2010, and Japanese Patent Application No. 2011-013538, filed on Jan. 26, 2011, including the specifications, claims, drawings, and abstracts, is directly incorporated by reference as a part of the application.

Industrial Applicability

The present invention is applicable to diagnosis assistance for thoracic movements and the like in the medical field.

The invention claimed is:

1. A diagnosis assistance information generating system comprising:
    an imaging unit structured to image a subject using a radiation source and a radiation detector structured to detect radiation which is irradiated from the radiation source and which is transmitted through the subject by a plurality of detection elements positioned two dimensionally to generate image data of the subject; and
    an image analysis unit structured to generate diagnosis assistance information regarding the subject abased on the image data acquired by the imaging unit;
    wherein, the imaging unit is able to successively irradiate radiation from the radiation source to acquire a plurality of frame images showing movement of the subject, the imaging unit further comprising:
    an anti-scattered radiation grid structured to remove scattered radiation from the radiation source; and
    an imaging control unit structured to control whether imaging is performed using the anti-scattered radiation grid;
    wherein, the imaging control unit is structured to control imaging to be performed without the anti-scattered radiation grid when diagnosis assistance information regarding the movement of the subject is generated by the image analysis unit.

2. The diagnosis assistance information generating system of claim 1, wherein the image analysis unit is structured to calculate signal changing amount based on the plurality of frame images acquired by the imaging unit and generate the diagnosis assistance information regarding the movement of the subject based on the calculated signal changing amount.

3. The diagnosis assistance information generating system of claim 1, wherein the imaging control unit is structured to control imaging to be performed with the anti-scattered radiation grid in static imaging.

4. The diagnosis assistance information generating system of claim 3, wherein the imaging control unit is structured to change a radiation irradiation condition depending on whether imaging is performed with the anti-scattered radiation grid or without the anti-scattered radiation grid.

5. The diagnosis assistance information generating system of claim 1, wherein the imaging control unit is structured to set a radiation irradiation condition so that an irradiation dose of one static imaging with the anti-scattered radiation grid is equal to a total irradiation dose of a series of dynamic imaging without the anti-scattered radiation grid.

* * * * *